(12) United States Patent
Martin et al.

(10) Patent No.: US 8,120,893 B2
(45) Date of Patent: Feb. 21, 2012

(54) TETHER-CONTAINING CONDUCTING POLYMERS

(75) Inventors: Brett D Martin, Washington, DC (US); Banahalli R Ratna, Alexandria, VA (US); Jawad Naciri, Herndon, VA (US); Michael A Markowitz, Springfield, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 381 days.

(21) Appl. No.: 12/564,270

(22) Filed: Sep. 22, 2009

(65) Prior Publication Data
US 2010/0073847 A1    Mar. 25, 2010

Related U.S. Application Data

(60) Provisional application No. 61/098,905, filed on Sep. 22, 2008.

(51) Int. Cl.
*H01G 9/00*    (2006.01)
(52) U.S. Cl. ........ 361/523; 361/516; 361/517; 361/519; 361/528; 361/529; 29/25.01; 29/25.03
(58) Field of Classification Search ............... 361/523, 361/516–517, 519, 525–529, 530; 438/584, 438/638; 29/25.01, 25.03
See application file for complete search history.

(56) References Cited

U.S. PATENT DOCUMENTS

| | | | |
|---|---|---|---|
| 4,978,780 A | 12/1990 | Fikentscher et al. | |
| 5,723,655 A * | 3/1998 | Uno et al. | 562/58 |
| 6,051,679 A | 4/2000 | Leclerc et al. | |
| 6,219,222 B1 | 4/2001 | Shah et al. | |
| 6,235,827 B1 * | 5/2001 | Kim et al. | 524/403 |
| 6,334,966 B1 * | 1/2002 | Hahn et al. | 252/500 |
| 6,665,169 B2 | 12/2003 | Tennent et al. | |
| 6,706,218 B2 | 3/2004 | Lucht et al. | |
| 6,794,110 B2 * | 9/2004 | Breyta et al. | 430/270.1 |
| 6,867,281 B2 * | 3/2005 | Martin et al. | 528/373 |
| 6,905,586 B2 | 6/2005 | Lee et al. | |
| 7,001,669 B2 | 2/2006 | Lu et al. | |
| 7,025,324 B1 | 4/2006 | Slocum et al. | |

(Continued)

OTHER PUBLICATIONS

Search Report and Written Opinion in PCT/US09/57790, Oct 28, 2009.

(Continued)

*Primary Examiner* — Nguyen T Ha
(74) *Attorney, Agent, or Firm* — Amy L. Ressing; Joseph T. Grunkemeyer

(57) ABSTRACT

A compound having the formula below. X is hydroxyl, a sulfonic ester or salt thereof, a phosphonate or salt thereof, a carboxylate or salt thereof, or a boronic ester or salt thereof. The value n is an integer greater than or equal to 2. A polymer made by polymerizing the compound. A method of: reacting $NH_2—(CH_2—CH_2—O)_n—CH_2—CH_2—OH$ with thiophene acid chloride to form a $(SC_4H_3)—CO—NH—(CH_2—CH_2—O)_n—CH_2—CH_2—OH$ amide; reacting the amide with a vinyl sulfonic ester, a vinyl phosphonate, a vinyl carboxylate, or a vinyl boronic ester to form an intermediate; and converting the intermediate to a salt form.

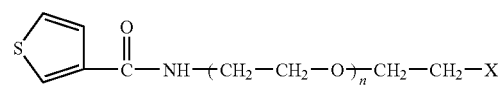

20 Claims, 17 Drawing Sheets

U.S. PATENT DOCUMENTS

| | | |
|---|---|---|
| 7,033,476 B2 | 4/2006 | Lee et al. |
| 2003/0088032 A1 | 5/2003 | Luebben et al. |
| 2007/0270508 A1* | 11/2007 | Liu .................................. 516/53 |
| 2008/0069971 A1 | 3/2008 | Keersmaecker et al. |
| 2008/0166564 A1 | 7/2008 | Rostovtsev et al. |
| 2008/0182844 A1 | 7/2008 | Bjergarde et al. |

OTHER PUBLICATIONS

Martin et al., "Conducting polymer "nanogates"—Controllable diffusivities in thin films of novel tether-containing sulfonated polythiophenes" Electrochemistry Communications 11 (2009) 169-173.

* cited by examiner

TETHER-CONTAINING CONDUCTING POLYMERS

This application claims the benefit of U.S. Provisional Application No. 61/098,905, filed on Sep. 22, 2008. The provisional application and all other publications and patent documents referred to throughout this nonprovisional application are incorporated herein by reference.

TECHNICAL FIELD

The present disclosure is generally related to conductive polymers.

DESCRIPTION OF RELATED ART

Extended π-conjugated electrically conducting oligomers and polymers have unique properties that have impacted diverse technologies, and have resulted in the appearance of new ones (Shirakawa et al., *Makromolec. Chemie*, 179, 6, (1978) 1565; Chiang et al., *J. Am. Chem. Soc.* (1978) 100, 1013). A partial list of applications includes micro- and nanoscale circuitry, throwaway electronic devices such as plastic electrochromic displays, flexible displays, lightweight storage batteries, corrosion protection coatings, antistatic coatings, bio- and chemical sensors, and military applications such as microwave-absorbing materials (MacDiarmid et al., *Makromol. Chem., Macromol. Symp.* 51 (1991) 11; U.S. Pat. No. 5,035,926; Pei et al., *Polymer* 35 (1994) 1347; Kumar et al., *Macromolecules* 29 (1996) 7629; Lu et al., *J. Appl. Phys.* 92 (2002) 6033).

Conducting polymers may exist in two chemically distinct states, "doped" (oxidized) and "dedoped" (reduced). The doped forms generally have a higher conductivity than the dedoped forms. In FIG. 1, two types of conducting polymers (polythiophene (PTP) and poly(3,4-ethylenedioxythiophene) (PEDOT)) are shown in both chemical states. The originating monomers are thiophene (TP) and 3,4-ethylenedioxythiophene (EDOT). The doped states contain radical cations (polarons), bipolarons, and are π-conjugated, with associated counterions. The dedoped states are electrically neutral and aromatic. The polymer is readily transformed from one state to the other in an electrochemical or chemical process. In an electrochemical transformation, an electrical bias ranging from −0.5 to 1.3 volts (vs. Ag/AgCl) is applied (Skotheim et al., Handbook of Conducting Polymers, Marcel Dekker, Inc., 1998; Groenendaal et al., *Adv. Mater.* 15(11) (2003) 855). The high voltage results in the appearance of the doped state; the low one, the dedoped state.

Each chemical state of the polymer may have properties that can make the materials useful as "switchable", reversible materials. PTP and PEDOT have been investigated as switchable electrochromic window materials (Cutler et al., *Macromolecules* 38(8) (2005) 3068). The conducting polymer polypyrrole has been successfully used as an electroactively switchable stationary-phase material for chromatography (Wallace et al., *Adv. Mat.* (2002) 14, 953; Ge et al., *J. Liq. Chromatography*, (1994), 17, 1301), and the conducting polymer polyaniline has been used as an electroactively switchable ion exchange resin for reduction and removal of hexavalent chromium (Ruotolo et al., *Reactive & Functional Polymers* 62 (2005) 141).

The attachment of lengthy side-chains to the conducting polymer main chains has in the past served diverse purposes such as 1) enhancement of polymer solubility (thus processability) (Zottio et al., *Macromol. Chem. Phys.* 203 (2002) 1958; Leclerc et al., *Synth. Met.*, 41 (2002) 529; Leclerc et al., *Adv. Mat.*, 9 (1997) 1087), 2) allowance of potentiometric detection of ligand binding (Emge et al. *Synth. Met.*, 84 (1997) 213; Nilsson et al., *Nature Materials*, 2 (2003) 419), and 3) induction of solvatochromism (Tashiro et al., *J. Polym. Sci. B-Polymer Physics*, 29 (1991) 1223; Roux et al., *Chem. Mater.* 6 (1994) 620), ionochromism (Lanzi et al., *Synth. Met.*, 89 (1997) 181; Sandstedt et al., *Chem. Mater.* 7 (1995) 1057) or thermochromism (Levesque et al., *Chem. Mater.* 8 (1996) 2843; Boldea et al., *Jour. Mat. Chem.* 9 (1999) 2133). The attachment of ion-terminated side-chains is used in the "self-doping" of conducting polymers, a process in which an anionic group (i.e. sulfonate) provides rapid charge neutralization when the polymer is electrochemically switched between oxidation states (Patil et al., *J. Am. Chem. Soc.* 109 (1987) 1858; Ikenoue et al., *J. Chem. Soc., Chem. Comm.*, 23 (1990) 1694).

The concept of controlling fluid flow on a nanoscale level has been termed "nanogating", and is starting to be explored through approaches such as piezoelectric gating of silica cantilevers (White et al., *Rev. Scientific Instr.* 74, 11, (2003)) and molecular simulations of controllable water flow through charged single-walled carbon nanotubes (Li et al., *Proc. Natl. Acad. Sci.* 104, 10, (2007) 3687). Often, the aim of these control strategies is to mimic the effect of biological membrane components (i.e., aquaporins) that are selective towards water molecules but prevent passage of protons.

Conducting polymers undergo major physical and chemical changes when oxidized (doped) and or reduced (dedoped). These changes are accompanied by charge neutralization processes in solution, involving ion movements to and from the polymer main chains. These mass transport processes are often highly complex, with the direction of motion dependent on ion charge, size, and solvation number. (Bilger et al., *Synth. Met.* 43 (1991) 2893; De Paoli et al., *Electrochemica Acta*, 37 (1992) 1173; Pei et al., *Solid State Ionics* 60 (1993) 161). Through appropriate molecular design, it may become possible to harness these polymer redox changes and ion transport processes to create a gating effect on the nanoscale. A recent investigation involving this approach was reported (Fletcher et al., *ACS Nano*, 2 (2008) 247), where polypyrrole with dodecylbenzene dopant was synthesized in the presence of anchored, vertically-aligned carbon nanotubes. It exhibited some diffusion gating effects that arose from the swelling and shrinking of the polymer that accompanies oxidation/reduction, although it was found that the material had a limited ability to undergo repeated be repeated cycling.

Electric double-layer capacitors, also known as supercapacitors, or electrochemical double layer capacitors (EDLCs), are electrochemical capacitors that are able to store charges in the electrode/electrolyte interface. They have a very high energy density when compared to common capacitors, typically on the order of thousands of times greater than a high-capacity electrolytic or dielectric capacitor. For example, a typical electrolytic or dielectric capacitor will have a storage capacity measured in microfarads, while the same sized electric double-layer capacitor stores several farads, an improvement of ~$10^4$ in capacitance, but usually at a lower working voltage. Larger commercial electric double-layer capacitors have capacities as high as 5,000 farads, with specific capacitances of ~5.1 farads/gram.

Supercapacitors fill an important and otherwise vacant niche in the current set of energy-storage devices, bridging the gap between batteries and conventional capacitors. They possess higher power densities than batteries, allowing them to perform a role in load-leveling of pulsed currents. They can help to improve battery performance when combined in hybrid power sources, or they can provide an efficient and long-lasting means of energy storage when used on their own.

One drawback in state-of-the art electrochemical supercapacitors is that they require liquid electrolyte for the ion-pairing associated with charge storage. The liquid contributes significantly to the weight of the device, and it tends to break down at higher voltages.

Porous carbon materials, especially mesoporous ones, are widely used for supercapacitor applications, because efficient charging of the electrical double layer requires materials with a high internal surface area and pore sizes that are similar to the size of the electrolyte ions (Frakowiak et al., *Carbon* 39 (2001) 937). The most suitable method for controllable preparation of carbons with appropriately sized, interconnected mesopores is the template method. It has resulted in great progress in the improvement of supercapacitor performance. Apart from the pure electrostatic attraction of ions, very often the capacitance of these materials can be enhanced by the presence of heteroatoms such as N and O in the carbon network. They are the origin of stable Faradaic reactions that make a substantial contribution to the capacitance in the form of "pseudocapacitance" (Jurewicz et al., *Fuel Process Technol.* (2002) 77-78, 191; Hulicova et al., *Chem. Mater.* (2005) 17, 1241; Lota et al., *Chem. Phys. Lett.* (2005) 404, 53). The liquid electrolyte may be aqueous, which limits the operational voltage to ~1 volt, or organic, which has an upper limit of ~2.2 volts.

Several types of conventional polymers, many of them inherently conducting, have been used to enhance the capacitance of these materials via pseudocapacitance. FIG. 19 (all but last bar on right) gives a summary of reported values of specific supercapacitance exhibited by several types of conventional conducting polymers in carbon supports, many of them mesoporous. The grey bars represent the capacitance of the entire material (farads/gram conducting polymer plus support), whereas the orange bars represent the capacitance of the active layer of conducting polymer itself (farads/gram conducting polymer). Clearly, ordered vs. disordered mesopore support structures allow for much higher values of capacitance (Dione et al., *Journal of Power Sources* 170 (2007) 441; Wang et al., *Adv. Mater.* (2006), 18, 2619-2623; Fan et al., *Adv. Funct. Mater.* (2007), 17, 16, 3083; Lota et al., *Journal of Physics and Chemistry of Solids* 65 (2004) 295-301; Selvakumar et al., *Jour. Appl. Polym. Sci,* 107, 2165-2170 (2008)). In all cases shown, the electrolyte was 1 M sulfuric acid, and the value shown is the highest value reported for the material studied.

BRIEF SUMMARY

Disclosed herein is a compound having the formula below. X is hydroxyl, a sulfonic ester or salt thereof, a phosphonate or salt thereof, a carboxylate or salt thereof, or a boronic ester or salt thereof. The value n is an integer greater than or equal to 2.

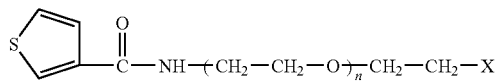

Also disclosed herein is a polymer made by polymerizing the above compound.

Also disclosed herein is a method comprising: reacting $NH_2$—$(CH_2$—$CH_2$—$O)_n$—$CH_2$—$CH_2$—$OH$ with thiophene acid chloride to form a $(SC_4H_3)$—$CO$—$NH$—$(CH_2$—$CH_2$—$O)_n$—$CH_2$—$CH_2$—$OH$ amide; reacting the amide with a vinyl sulfonic ester, a vinyl phosphonate, a vinyl carboxylate, or a vinyl boronic ester to form an intermediate; and converting the intermediate to a salt form. The value n is an integer greater than or equal to 1.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
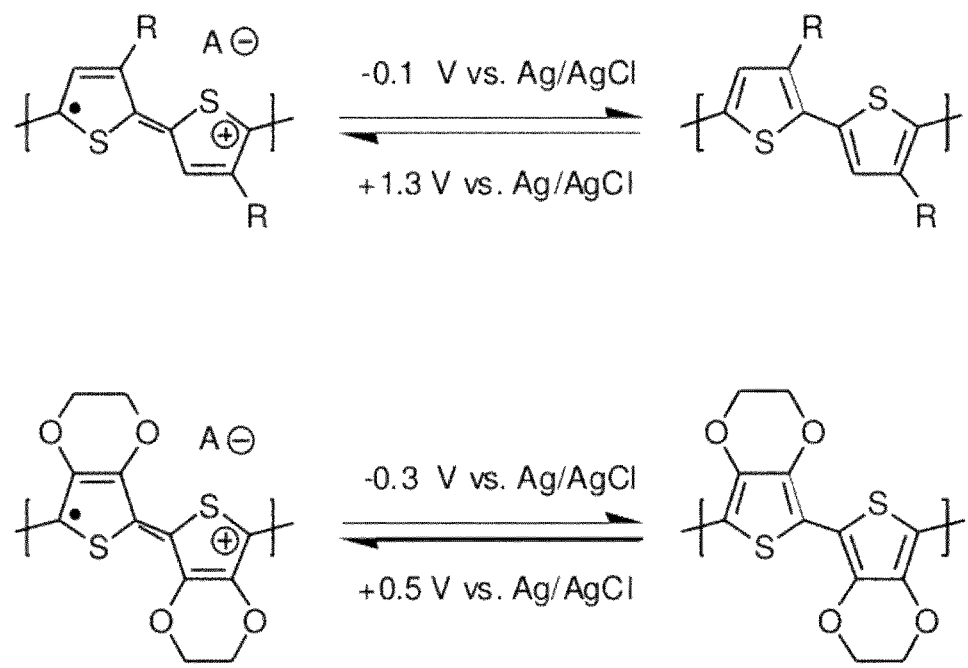
FIG. 1 shows doped and dedoped states of PTP and PEDOT, and the redox potentials associated with the state changes. R is often alkoxy or alkyl.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is the synthesis and characterization of atypical tether-containing polythiophenes, such as poly(thiophene-3-carboxylic acid 2-(2-(2-(2-ethoxy-ethoxymethyl sulfonate)-ethoxy)-ethoxy)-amide, hereafter referred to as poly(TP—OEG-SO$_4$). The polymer can exhibit an active, reversible nanoscale gating effect that has been substantially characterized. Cyclic voltammetry data permit calculating liquid-phase ion diffusivities in the polymer as a function of its oxidation state. Diffusivities may be more than 350 times higher in the oxidized state versus the reduced state. As a control, the nontethered poly(3',4'-dimethyl-[2,2';5',2"]terthiophene) (DMPT) was synthesized and characterized. On comparing both polymers in the reduced state, diffusivities in poly(TP—OEG-SO$_4$) were found to be more than 4500 times lower than in poly(DMPT). To explain this behavior, a model is proposed that features a charge-balancing mechanism by the sulfonate tethers in poly(TP—OEG-SO$_4$), which causes nanoporous regions around the polymer main chains to be opened and closed, leading to the large observed differences in diffusivities. These data suggest that the polymer poly(TP—OEG-SO$_4$) is evidently able to act as a reversible "nanogate" with an open pore structure when oxidized, and a closed one when reduced. Such a reversible material may have diverse uses in threat protection, separations, nanotechnology, nanodevices, nanofluidics, and manufacturing on the nanoscale.

The polymer contains long, charged, anchored tethers that may intramolecularly ion-pair to provide charge neutralization to the polymer when it is in its oxidized (doped) state. When the polymer is switched to its reduced (dedoped) state, the freed tethers are allowed to "random walk" in the surrounding nanoregions, and thus obstruct movement of liquid or solute. Thus the tethers serve as "nanogates" that are open when the polymer is oxidized, and closed when the polymer is reduced. The switching of the redox states is reversible, and actuated by the application of small voltages (0 to 1.5 volts). This effect is reversible over a large number of cycles.

It has also been found that poly(TP—OEG-SO$_4$) can be electrochemically formed as a thin film on the interior pore walls of conducting, ordered mesoporous materials such as those composed of templated carbon-silica. When used in this manner as an activating layer in the conducting mesoporous support, the polymer may exhibit a very high specific capacitance of 1500-2000 and up to 2570 Farads/gram polymer·M electrolyte. Thus, poly(TP—OEG-SO$_4$) may aid in the creation and development of a lightweight, nanocomposite supercapacitor material having high energy/power density. It may be useful for energy storage/generation, power conditioning, pulsed power delivery, nanoelectronics, and other electrical applications.

The monomer containing the charged sulfonate tether can act as a "nanogate." Its chemical name is (thiophene-3-carboxylic acid 2-(2-(2-(2-ethoxy-ethoxymethyl sulfonate)-ethoxy)-ethoxy)-amide, and will be hereafter referred to as TP—OEG-SO$_4$. TP—OEG-SO$_4$ was copolymerized with the commercially-available monomer thiophene-3-phenol; electrochemical analysis showing that the presence of the tether both lowered electrolyte diffusion D significantly (by a factor of 13.5), and enhanced the reversibility of the oxidation/reduction processes of the polymer, when compared to polymer prepared from thiophene-3-phenol only. TP—OEG-SO$_4$ was copolymerized with the in-house synthesized terpolymer poly(3',4'-dimethyl-[2,2';5',2"]terthiophene) (poly(DMTP)). Electrochemical analysis showed that the presence of the tether improved the ability of the polymer to be oxidized and reduced in both the presence and absence of solute electrolyte, when compared to polymer prepared from DMPT only. These results were the first indications that the anionic sulfonate that terminates the tether is actively participating in ion-pairing with the cations that are present in the polymer main chains when the polymer is in its oxidized state. Electropolymerization of TP—OEG-SO$_4$ and TP—OEG-SO$_4$ with DMPT was performed, and electrochemical analysis was performed using the Randles-Sevcik equation. This allowed calculation of anion diffusivities D as a function of polymer oxidation state. It was found that D of the tethered sulfonate can be three orders of magnitude higher when the polymer is in its doped state (while experiencing the peak oxidation current) vs. when in the dedoped state (while experiencing the peak reduction current). Further cyclic voltammetry studies were performed on poly(TP—OEG-SO$_4$) and poly(DMTP), which showed significant differences in their electrochemical behavior. For poly(TP—OEG-SO$_4$), it was also found that D was as much as 350 times higher in the doped (oxidized) state versus the dedoped (reduced) state. On comparing poly(TP—OEG-SO$_4$) and poly(DMTP) with both polymers in the dedoped (reduced) state, diffusivities in poly(TP—OEG-SO$_4$) were found to be as much as than 4500 times lower than in poly(DMPT). Finally, TEM images of the poly(TP—OEG-SO$_4$) were acquired in the doped (oxidized) state and the dedoped (reduced) state. The pore sizes of the polymer are clearly much larger when the polymer is in its doped state vs. the dedoped state.

Developments in nanotechnology have occurred at a very past pace in the past several years, and the selective control of diffusion at the nanoscale level is expected to be of high importance in many scenarios. For example, a material capable of reversibly switching from an open, permeable state to a closed, impermeable state clearly has key importance in the area of chemical/biological warfare protection.

Other applications for such a material include, but are not limited to, water purification, smart filtration, high-selectivity separation of chemical compounds, isolation of single molecules, gating of nanofluidic flow, nanomanufacturing, and special problems in nanobiotechnology. Disclosed herein is reversible electrochemical/electrical control over the diffusivities of ionic solutes via a mechanical gating mechanism involving the novel tether-containing conducting polymer poly(TP—OEG-SO$_4$). It is highly likely that its mechanism will also operate well in pure gas or pure liquids not containing solute.

In energy storage technology, electrochemical supercapacitors complement batteries and have capacitances several orders of magnitude higher than conventional dielectric capacitors. When present as a thin layer in the ordered mesopores of a conducting carbon-silica nanocomposite, poly(TP—OEG-SO$_4$) displays an extremely high specific electrochemical supercapacitance. Thus it has potential applications as a new supercapacitive material. State-of-the art electrochemical supercapacitors require liquid electrolyte for the ion-pairing associated with charge storage. The liquid contributes significantly to the weight of the device, and it tends to break down at higher voltages. A potential advantage of the tether element in poly(TP—OEG-SO$_4$) is that it may provide an intramolecular ion-pairing capability that will allow total replacement of liquid electrolyte. The polymer tethers may allow a much more efficient, rapid discharge of current since the anionic tether end-group will be only a few nm distant from the cationic center on the conducting polymer main chain that it serves to neutralize. No diffusion of electrolyte in free liquid is involved. Its replacement by the tether will thus result in a lightweight supercapacitive material that will can significantly higher operating voltages than those that constrain state-of-the-art supercapacitors.

The poly(TP—OEG-SO$_4$) may address needs for smaller, lighter capacitors with higher energy and power densities. Also, future capacitor materials must be rugged, have rapid discharge rates, sustain charge over long time periods, and be environmentally friendly. The material is very well suited to contribute to these needs. Its development supplements interests in the capacitor materials area which include improved synthesis of olefinic polymers, polar polymers, and nanocomposite approaches.

The ability to be cycled between the oxidized, open state and the reduced, closed state at low voltages (between 0 and 1.5 volts vs. Ag wire) rather than higher ones may be an asset. Regarding supercapacitance, it is important to note that state-of-the art electrochemical supercapacitors require liquid electrolyte for the ion-pairing associated with charge storage. The liquid contributes significantly to the weight of the device, and it tends to break down at higher voltages. A potential advantage of the tether element in poly(TP—OEG-SO$_4$) is that it provides an intramolecular ion-pairing capability that may allow total replacement of liquid electrolyte. The polymer tethers may allow a more efficient, rapid discharge of current since the anionic tether end-group will be only a few nm distant from the cationic center on the conducting polymer main chain that it serves to neutralize. No diffusion of electrolyte in free liquid is involved. Its replacement by the tether may thus result in a lightweight supercapacitive material that will have significantly higher operating voltages than those that constrain state-of-the-art supercapacitors.

Figure 2:
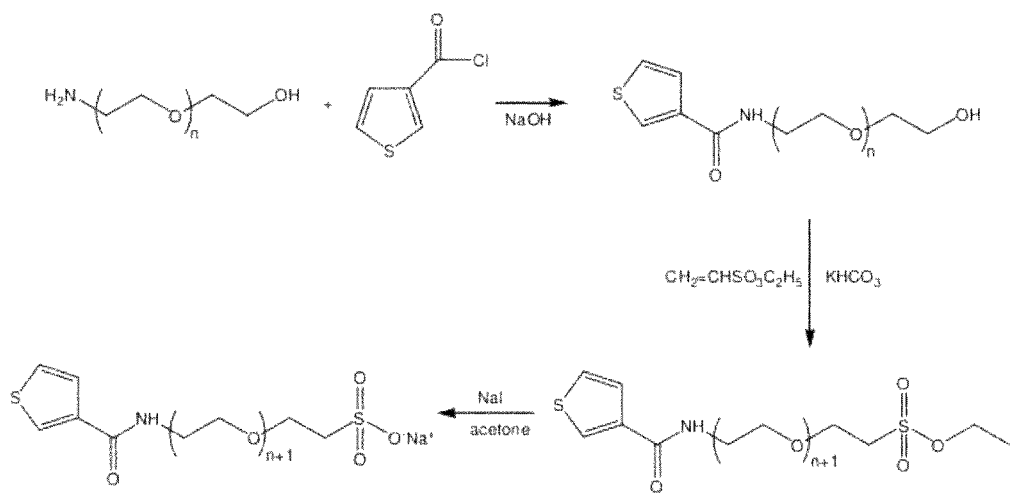
FIG. 2 shows one synthetic scheme for the disclosed monomers.

The monomers may be synthesized according to the scheme shown in FIG. 2. The value n may be 1 or more, and may be from 1 to 9, or may be 3 as in the examples below. The vinyl sulfonic ester may have an ethyl group or any other organic group that allows the reaction to proceed. A phosphonate (—PO(OR)$_2$), a carboxylate (—CO$_2$R), or a boronic ester (—B(OH)(OR) may be used according to synthetic techniques known in the art, instead of the sulfonate ester (SO$_3$R) shown in FIG. 2.

The salt form thiophene monomers may be polymerized according to techniques known in the art and as exemplified below. The doped and dedoped forms are shown below, where m is a positive integer in either case, and where R is the tether group, including but not limited to —CO—NH—(CH$_2$—CH$_2$—O)$_n$—CH$_2$—CH$_2$—SO$_3^+$. Note that in any depiction herein of anions, the anion may be associated with a cation such as Na$^+$. The orientation of the thiophene groups may vary, such that any tether groups may be bound to the 3- or 4-position of the thiophene ring. The dedoped form may also be depicted as repeat unit containing 4 thiophene monomers. The tether compound may also be copolymerized with a second monomer that may form a conductive polymer. Such monomers are known in the art and include, but are not limited to, thiophene and substituted thiophene.

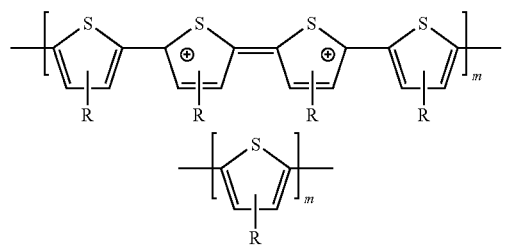

Figure 3A:
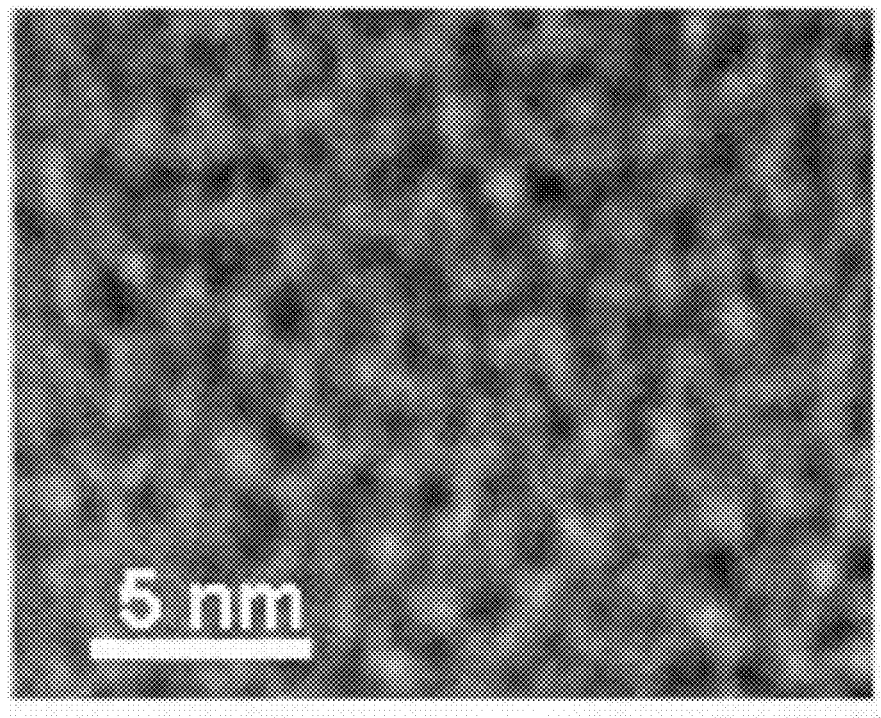
FIG. 3 shows TEMs of the closed (a) and open (b) states of a nanogate.
Figure 4:
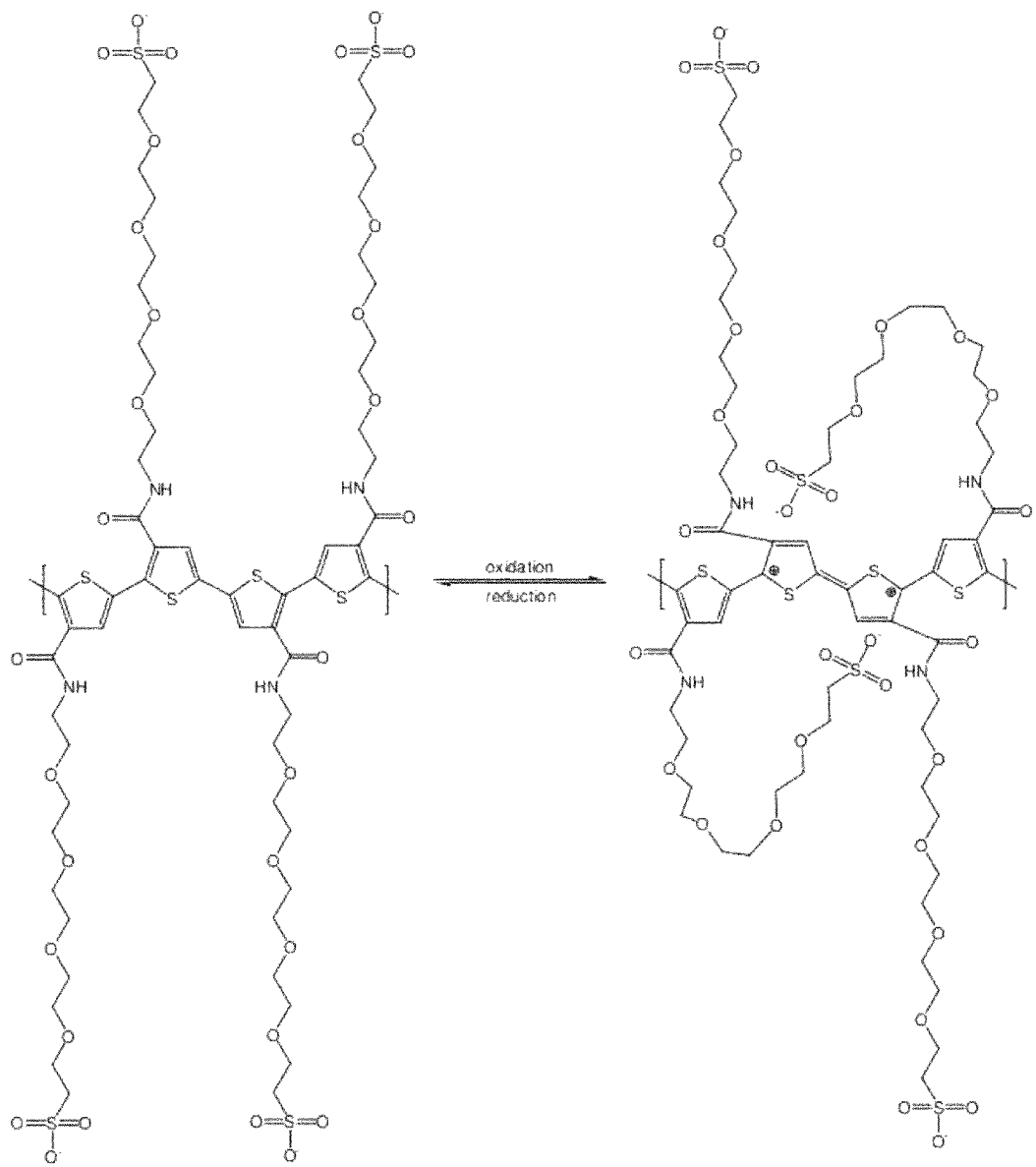
FIG. 4 shows the proposed charge-balancing mechanism by sulfonate tethers.

The structure of the resulting "comb" polymer, poly(TP—OEG-SO$_4$), is shown in FIG. 4. It will be assumed that the polymerization occurs predominately via the 2- and 5-positions since the 4-position in these types of structures compounds is normally not as reactive towards C—C bond formation. The proposed mechanism of charge balancing through tether movement is also shown in FIG. 4, with the resulting influences on the surrounding nanoscale space apparent. Transmission electron microscope (TEM) images of the polymer in the reduced and oxidized states are shown in FIGS. 3(a) and (b). They clearly indicate that the polymer fine structure changes with oxidation state, with porous regions (lighter areas) becoming significantly larger when the polymer is switched into its oxidized form. As the sulfonate tethers form intra-molecular ion pairs, they vacate the regions farther away from the polymer main chains and cause the electron density there to drop. Simultaneously, the darker regions (which correspond to polymer-rich regions), become enlarged. The tethers may concentrate next to the polymer main chains, thus increasing the local electron density. The polymer may assemble into larger aggregates when oxidized because as the sulfonate tethers form intra-molecular ion pairs, the number of repulsive inter-chain anion-anion interactions is lowered. This may permit closer chain packing. However, since some of the tethers remain unpaired, the overall network-like structure of the polymer is retained as its state is switched. In the oxidized state, the porous regions may be large enough to easily transport solvated electrolyte or tether ions—the corresponding regions in the reduced state may be too constricted to allow efficient transport.

For nanogating and supercapacitor applications, a copolymer can be formed from TP—OEG-SO$_4$ and DMPT. In this architecture, the tether moieties will be present at a lower density than in the homopolymer poly(TP—OEG-SO$_4$). They may experience a greater freedom of movement and thus may undergo a more efficient intramolecular ion-pairing. A crosslinker based on two 3,4-ethylenedioxythiophene (EDOT) moieties connected via an adipic acid moiety may be used. An EDOT crosslinker may contribute to the mechanical strength of the polymer and prevent liquid-phase dissolution of the poly(TP—OEG-SO$_4$) chains.

A capacitor may be made by placing a material comprising the disclosed polymers between and anode and a cathode. Any configuration of the capacitor may be made that results in a capacitance between the anode and cathode. Such configurations are known in the art. The material may be a mesoporous carbon support having the polymer coating the pores, as described below.

Poly(TP—OEG-SO$_4$) may also be synthesized within a polyurethane matrix, forming a molecular architecture described by the phrase "interpenetrating network" (IPN). The polyurethane Estane MVT 75 (BF Goodrich) may be compatible with the poly(TP—OEG-SO$_4$) polymerization and redox chemistries. It may further increase the mechanical strength and processability of the material. Estane MVT 75 is also known for its high moisture vapor transport capabilities.

The IPN components may be chosen for chemical and environmental stability and physicochemical compatibility. For example, polythiophene is chemically stable in both its oxidized ("doped") and reduced ("dedoped") states. Also, the EDOT-based crosslinker is readily copolymerized with the TP—OEG-SO$_4$ monomer. The second IPN constituent (MVT 75 polyurethane), is a thermoplastic polymer based on aromatic and oligoethyleneglycol repeat units. The mutual presence of the oligoethyleneglycol chain segments and ether functionalities affords chemical compatibility between the three components.

The polymer may be used in a nanogate by oxidizing and reducing a material comprising the polymer. The oxidation increases the diffusivity of the material and the reduction decreases it. The cycle can be repeated any number of times.

The following examples are given to illustrate specific applications. These specific examples are not intended to limit the scope of the disclosure in this application.

Example 1

Chemical synthesis of TP—OEG-SO$_4$ and DMTP—Solvents, gold wire, and precursors for the conducting polymers were purchased from Sigma-Aldrich. The monomer TP—OEG-SO$_4$ was synthesized in four steps (FIG. 2). To form the tether precursor amide (Eq. (2)), a mixture (2.5 g, 19.5 mmol) of thiophene carboxylic acid, a molar excess of oxalyl chloride, and 1 drop of DMF in 10 mL of benzene was stirred overnight at room temperature (Marchand-Brynaert et al., *Tetrahedron*, 52 (1996) 5591). The solvent was removed under vacuum and the resulting residue was dissolved in THF. This solution was added dropwise at 0° C. to a stirred mixture of PEG-amine (Eq. (1)) (3.05 g, 16.0 mmol) in 50 mL of water and 1.28 g of NaOH. The reaction was stirred overnight at room temperature. The solution was acidified to a pH 4.0 with 1 N HCl solution. Extraction with ethyl acetate gave a yellow liquid. Gradient column chromatography in silica with ethyl acetate eluent followed by methanol yielded 2 g of the final product amide as a viscous liquid. To synthesize the tether derivative intermediate (Eq. (3)), a mixture of amide (2 g, 6.60 mmol), vinyl ethyl sulfonate (0.89 g, 6.60 mmol), and 0.13 mg of KHCO$_3$ in 20 mL of acetonitrile was heated to 80° C. for 3 days. Filtration of the solution and evaporation of the solvent led to a yellowish oil. Purification was performed using silica gel with MeOH/CH$_2$Cl$_2$2/98 eluent. The final product was obtained as an oil (yield 1.2 g) and was characterized by $^1$H and $^{13}$C NMR. A mixture of the intermediate (0.8 g, 1.81 mmol) and NaI (0.30 g) in acetone was stirred overnight at room temperature. The solvent was evaporated and the product was washed with hexane. The final product TP—OEG-SO$_4$ (Eq. (4)) was dried under vacuum.

The monomer 3',4'-dimethyl-[2,2';5',2"]terthiophene was synthesized in a manner similar to that described in (Blondin et al., *Macromolecules* (2000) 33, 5874; Wang et al., *Chem. Mater.* (1994) 6401). Its structure is shown in Eq (5).

(1)

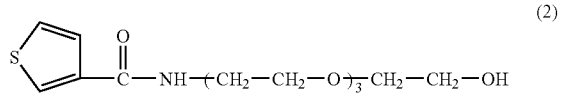

(2)

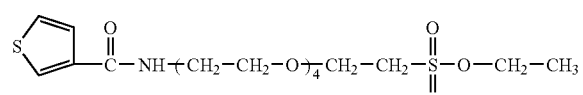

(3)

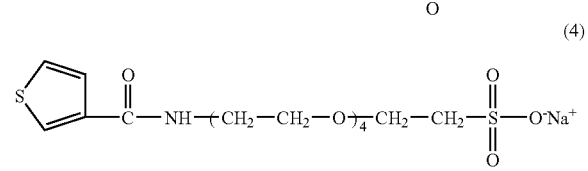

(4)

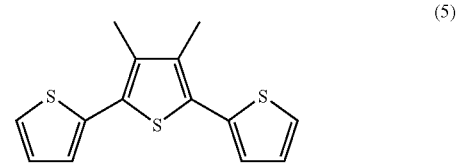

(5)

Example 2

Electrochemical Synthesis of poly(TP—OEG-SO$_4$) and poly(DMTP)—Dissolution of 15 mg TP—OEG-SO$_4$ into 4:1 toluene:acetonitrile (v:v) containing 200 mM t-butylammonium hexafluorophosphate was followed by electropolymerization into a thin film onto a 0.2 mm diameter gold coil with a 1 cm$^2$ immersion area using brief applications (90 seconds each) of 1.8 V vs. silver wire (power source CHI 660C Electrochemical Workstation, CH Instruments, Austin, Tex.). This particular solvent mixture was chosen because it supported the monomer as solute but the polymeric thin film had only a minimal solubility. A series of four applications of 1.8 V resulted in the deposition of 0.19 mg poly(TP—OEG-SO$_4$) onto the gold coil, determined gravimetrically and by coulometry. In a similar manner, DMTP was electropolymerized onto a gold coil, forming a thin film of mass 0.30 mg. Cyclic voltammetry studies were performed at 18° C. in a sealed cell using a CHI 660C Workstation, in the solvent system 4:1 toluene:acetonitrile (v:v) containing concentrations of t-butylammonium hexafluorophosphate ranging from 300 mM to 0.1 mM.

Example 3

Figure 3B:
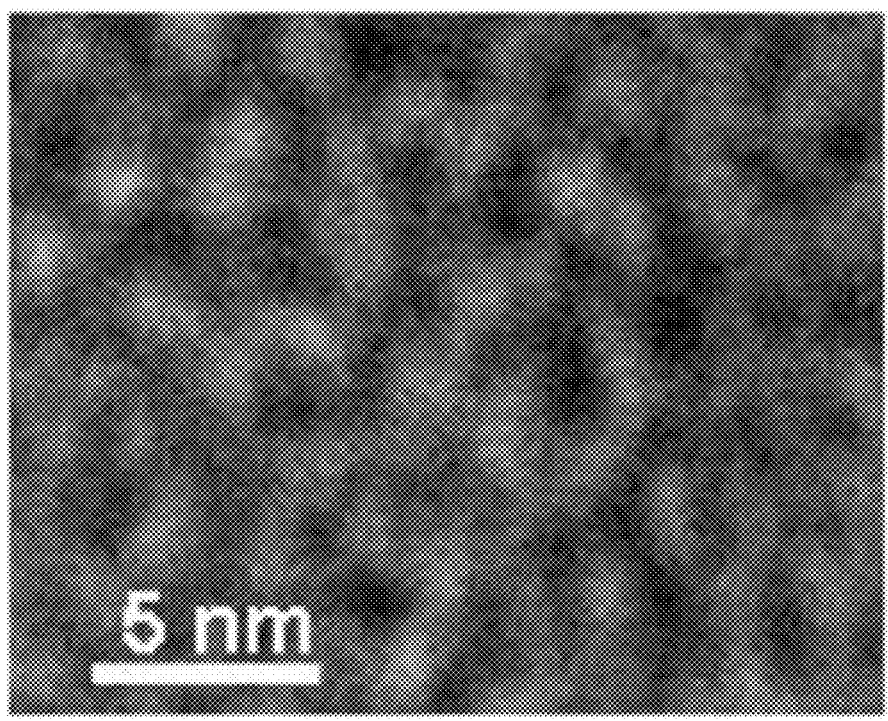

TEM of polymers—Monomer was electropolymerized onto copper TEM grids in a manner similar to that described above. The grids were washed to remove dried salts, and viewed with a transmission electron microscope (Libra 120, Carl Zeiss SMT, Peabody, Mass.) at 120 kV. Images were captured on a bottom-mounted digital camera (Olympus SIS, Montvale, N.J.). FIG. 3 shows TEMs of the closed (a) and open (b) states. They clearly indicate that the polymer fine structure changes with oxidation state, with porous regions (lighter areas) becoming significantly larger when the polymer is switched into its oxidized form. If the sulfonate tethers form intra-molecular ion pairs, they would vacate the regions farther away from the polymer main chains and cause the electron density there to drop. Simultaneously, the darker regions (which correspond to polymer-rich regions), would become enlarged. This is, in fact, what is seen in the image. The polymer may assemble into larger aggregates when oxidized because as the sulfonate tethers form intra-molecular ion pairs, the number of repulsive inter-chain anion-anion interactions is lowered. This would permit closer chain packing. However, since some of the tethers remain unpaired, the overall network-like structure of the polymer is retained as its state is switched. In the oxidized state, the porous regions may be large enough to easily transport solvated electrolyte or tether ions, with the corresponding regions in the reduced state being too constricted to allow efficient transport.

Example 4

Nanogating by poly(TP—OEG-SO$_4$)—For quantification of the nanoscale gating effects, the polymer was characterized using cyclic voltammetry and information was extracted describing the behavior of the sulfonate tether and solute, including their diffusivities during the peak oxidation and reduction currents. To accomplish this the Randles-Sevcik equation was used, which relates D to peak current ($i_p$), $$i_p = (0.4463)nFAC_0^*\left(\frac{nFvD}{RT}\right)^{0.5}$$

Where n=number of electrons, F=Faraday's constant, A=electrode area (cm$^2$), $C^*_0$=concentration of electrolyte (mole/cm$^3$), v=scan rate (volts/sec), D=diffusivity of the electrolyte in the polymer film (cm$^2$/s), R=universal gas constant, and T=temperature in Kelvins, with the assumption that the charge-compensation step is rate-limiting. It should be noted that the electrochemical determination of D in conducting polymer films can have caveats (Penner et al., *J. Phys. Chem.*, 92 (1988) 5274). However, the assumptions behind the Randles-Sevcik equation hold for the system in both oxidation states, and the analysis below deals exclusively with ratios of D, not absolute values.

It was anticipated that these diffusivities would reflect the degree of molecular crowding in the nanoporous regions surrounding the polymer backbone. The ratios of these diffusivities would be a quantification of the polymer's ability to act as an open nanogate (in the oxidized, doped state) or a closed one (in the reduced, dedoped state). To allow direct comparison of diffusivities in poly(TP—OEG-SO$_4$) with those in an untethered thiophene, similar cyclic voltammetric studies were performed on poly (DMTP). The comparisons have reinforced the model for nanopore opening and closing that is shown in FIG. 4.

Figure 5A:
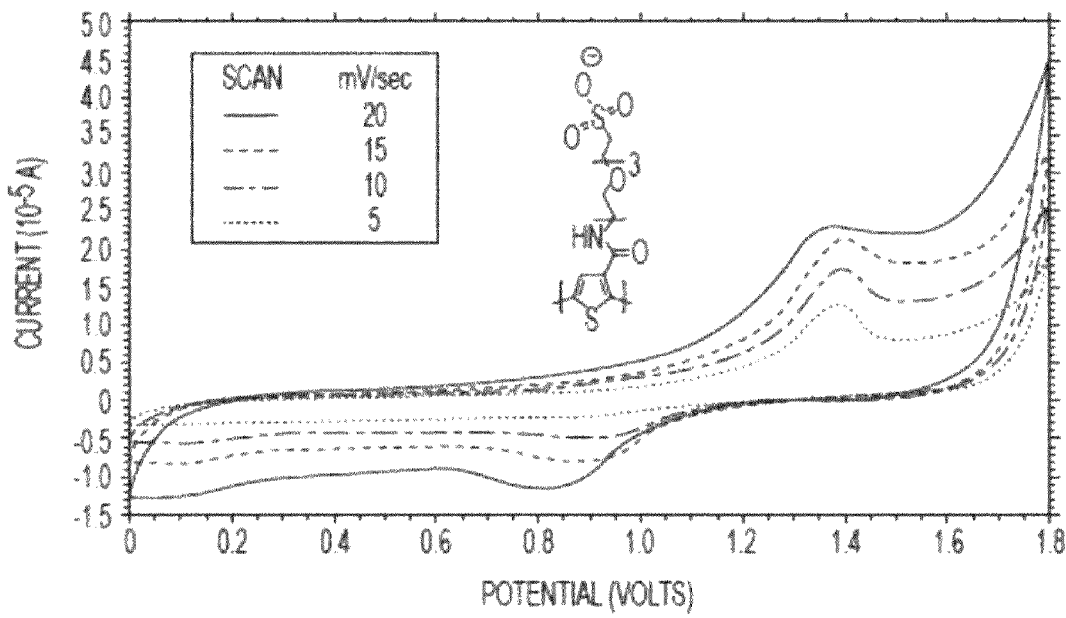
FIG. 5 shows cyclic voltammograms of poly(TP—OEG-SO$_4$) (a) and poly(DMTP) (b) as a function of scan rate, in the presence of 100 mM electrolyte.
Figure 5B:
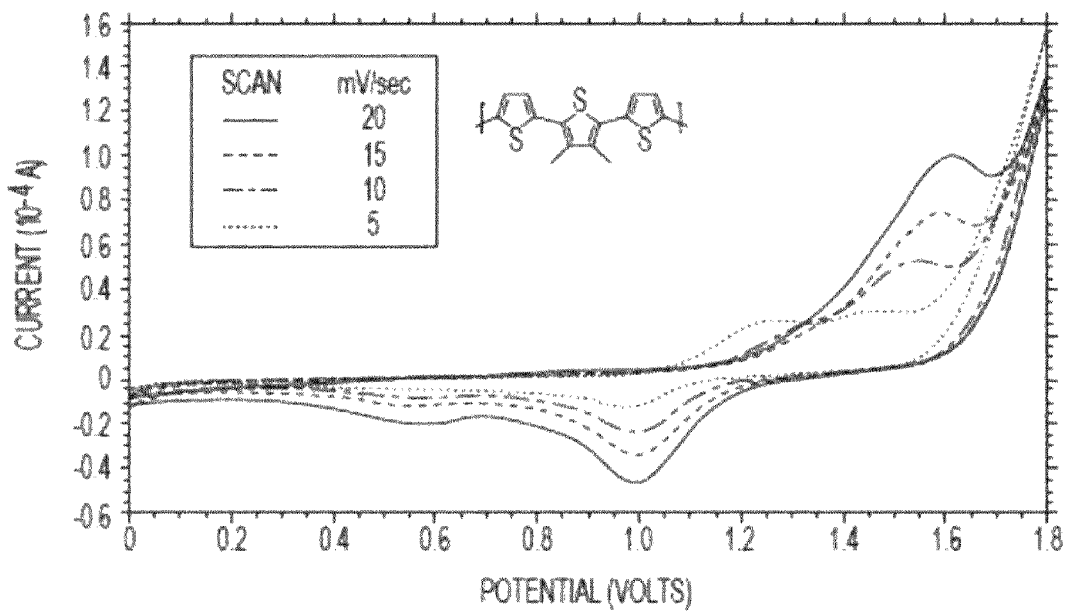
Figure 6A:
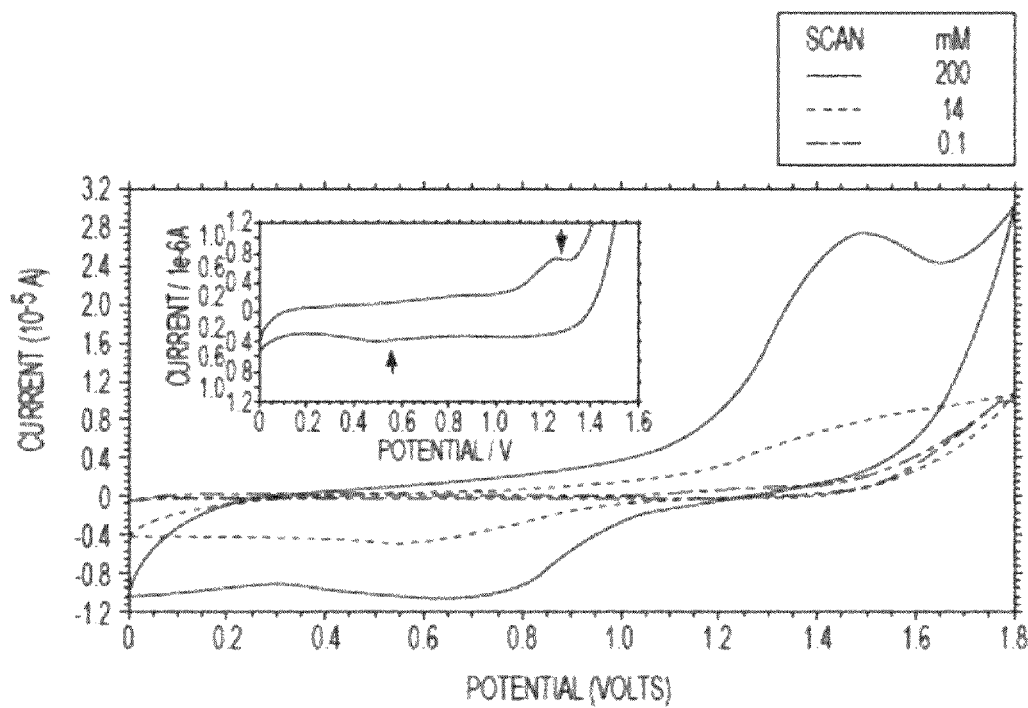
FIG. 6 shows cyclic voltammograms of poly(TP—OEG-SO$_4$) (a) and poly(DMTP) (b), at a scan rate of 10 mV/s and electrolyte concentrations of 200 mM (red), 14 mM (blue), and 0.1 mM (maroon).
Figure 6B:
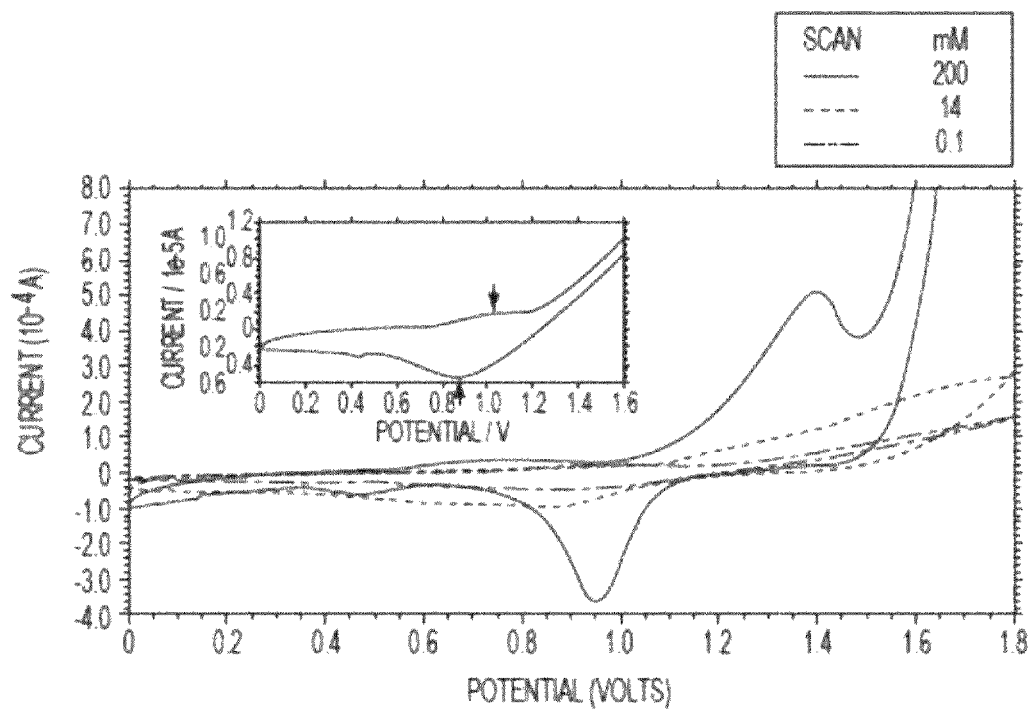

FIG. 5(*a*) shows the cyclic voltammogram of poly(TP—OEG-SO$_4$) using an electrolyte concentration of 100 mM, and scan rates ranging from 5 to 20 mV/sec. As expected, faster scan rates lead to systematic increases in the peak oxidation and reduction currents. FIG. 5(*b*) shows the analogous voltammogram of poly(DMTP). For each polymer, each complete scan was reproducible up to ten times. FIGS. 6(*a*) and (*b*) show representative cyclic voltammograms of the polymers at a scan rate of 10 mV/sec, with 200 mM electrolyte (red), 14 mM electrolyte (blue), and 0.1 mM electrolyte (maroon). Magnified views of the latter are shown in the inset. The arrows denote peak locations. For poly(TP—OEG-SO$_4$), as the electrolyte concentration is reduced towards trace levels the sharpness of the peaks decrease but their ΔEp is maintained, along with a high level of capacitive current. For poly(DMTP) the AEp of the peaks is greatly diminished, and the capacitive current is much lower. It is of interest that for poly(DMTP) a 2000-fold decrease in electrolyte concentration leads to a 340 and 65-fold decrease in oxidation and reduction currents, respectively. However, for poly(TP—OEG-SO$_4$) the corresponding decreases are only 38.6 and 23.3-fold. This is further evidence that the sulfonate tethers are substantially involved in ion-pairing processes that allow for electron release from the conducting polymer.

Figure 7A:
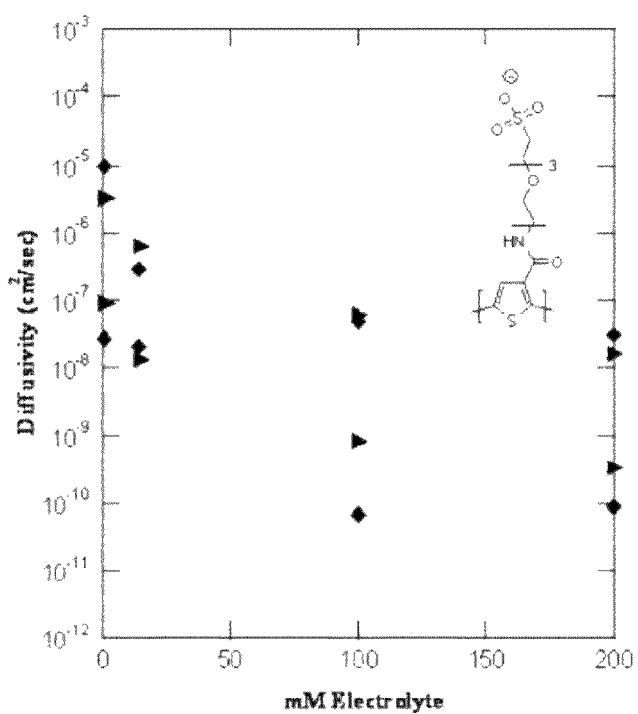
FIG. 7 shows logarithmic plots of global ion diffusivities D as a function of electrolyte concentration calculated for the tether polymer poly(TP—OEG-SO$_4$) (a) and poly(DMTP) (b). (Red diamonds, oxidized state at 5 mV/sec; orange triangles, oxidized state at 20 mV/sec; green diamonds, reduced state at 5 mV/sec; blue triangles, reduced state at 20 mV/sec)
Figure 7B:
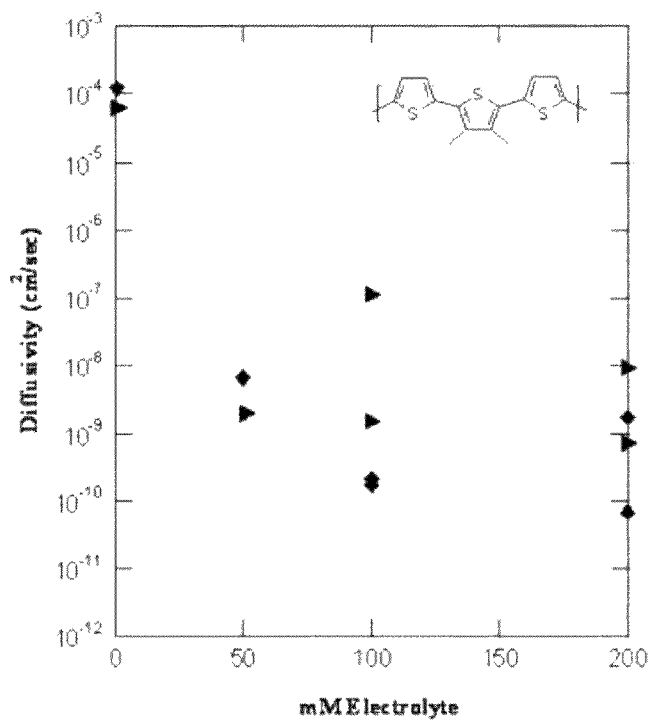

FIG. 7 depicts the logarithmic plots of global ion diffusivities D as a function of electrolyte concentration, which were calculated using the Randles-Sevcik equation and oxidation and reduction peak characteristics. In this context "global" refers to tethered sulfonate plus hexafluorophosphate. For poly(TP—OEG-SO$_4$) in the oxidized state, the values ranged from 10$^{-8}$ cm$^2$/sec to 10$^{-5}$ cm$^2$/sec; in the reduced state, from 10$^{-10}$ cm$^2$/sec to 10$^{-7}$ cm$^2$/sec. For poly(DMTP) in the oxidized state, the range is from 10$^{-9}$ cm$^2$/sec to 10$^{-4}$ cm$^2$/sec; in the reduced state, from 10$^{-10}$ cm$^2$/sec to 10$^{-4}$ cm$^2$/sec. For both states, the poly(TP—OEG-SO$_4$) shows an increase in D as electrolyte concentration is decreased. This rise may occur because electrostatic solute-solute interactions and double-layer effects are diminished as the solution becomes more dilute, and the ions experience diffusive pathways that are less complex. Extrapolation to zero mM electrolyte yields the diffusivity of the tethered sulfonate itself, as will be discussed below. In the reduced state, poly(DMPT) shows an even larger increase in D as electrolyte concentration is decreased. This may be because this polymer has a much less complex structure than the comb-type poly(TP—OEG-SO$_4$) and thus affords much simpler diffusive pathways to and from the main chain.

During oxidation of poly(TP—OEG-SO$_4$) the slowest scan rate (5 mV/sec) led to a ~3-fold higher diffusivity than the fastest rate (20 mV/sec), but during reduction it led to a ~3.5-fold lower diffusivity. This finding supports a model where a subpopulation of the tethered sulfonates, when given enough time, are able to organize and efficiently ion-pair with the polymer backbone and open nanopores in the surrounding molecular space, permitting fast diffusion of the remaining tethered sulfonates as well as PF$_6$ electrolyte. During reduction the slow scan rate also allows time for the ion-paired tethers to be released in an organized manner, which allows them to be very effective in blocking the nanopores in the surrounding space, dramatically slowing the diffusion of the remaining tethered sulfonates and PF$_6$ electrolyte. The rapid scan rate of 20 mV/sec may not allow sufficient time for this organizational process. In contrast, reduction of poly(DMPT) shows much less difference between the two scan rates.

Figure 8:
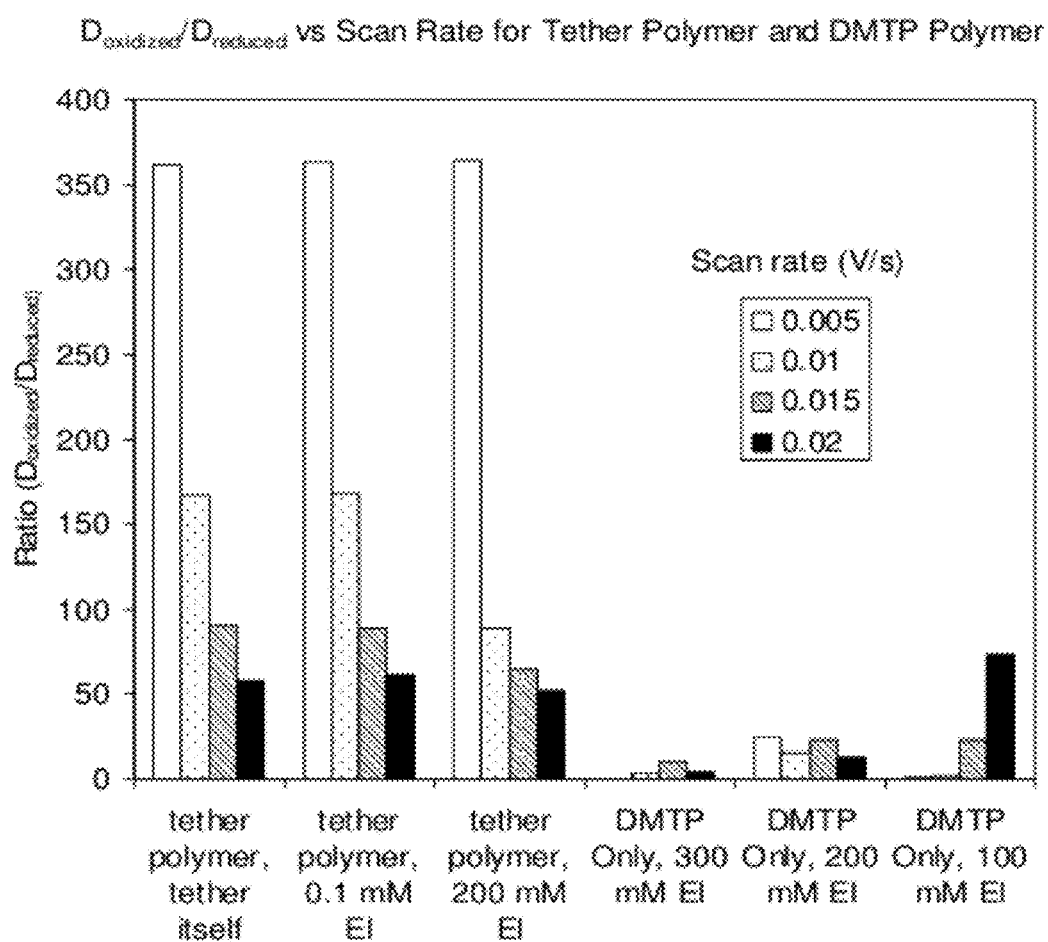
FIG. 8 shows the ratio $D_{oxidation}/D_{reduction}$ as a function of polymer type, scan rate, and electrolyte concentration.

In FIG. 8, the ratios $D_{oxidation}/D_{reduction}$ as a function of polymer type, scan rate, and electrolyte concentration are given. For poly(TP—OEG-SO$_4$), the ratio for the tethered sulfonate itself was obtained from FIG. 7 by extrapolation to zero mM electrolyte. For this polymer it is quite significant that at the slowest scan rate (5 mV/sec) the ratios converge to a universal value of 363 for all electrolyte concentrations, with a miniscule standard deviation of only 0.85. The fact that the ratio $D_{oxidation}/D_{reduction}$ increases steadily from ~57 to 363 as the scan rate is lowered from 20 mV/sec to 5 mV/sec provides further support for the proposed model where, if given sufficient time for organization, the tethers are able to open the nearby nanoporous regions when the polymer is undergoing oxidation and close these regions when reduction is occurring, and thus act as highly effective nanogates. The fact that a universal value (363) is reached, independent of electrolyte concentration, suggests that the diffusivities are controlled by a phenomenon of mechanical obstruction and clearance, rather than one involving complex ionic interactions such as double-layer formation. In stark contrast, the poly(DMPT) does not show this behavior at any of the electrolyte concentrations studied, with most of the $D_{oxidation}/D_{reduction}$ ratios falling between 1 and 20 with no systematic changes as a function of scan rate.

Figure 9:
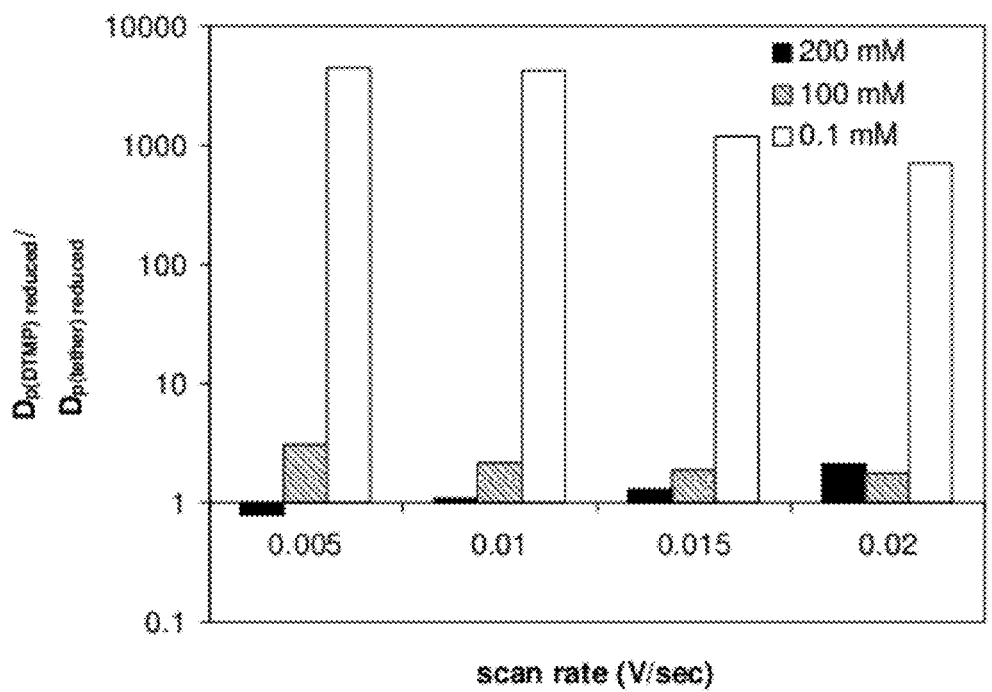
FIG. 9 shows the ratio $D_{p(DTMP)reduced}/D_{p(TP-OEG-SO4)reduced}$ as a function of scan rate and electrolyte concentration.

FIG. 9 shows the ratios of $D_{p(DTMP)reduced}/D_{p(tether)reduced}$ as a function of scan rate and electrolyte concentration. The term $D_{p(DTMP)reduced}$ represents global ion diffusivity in the poly(DMTP) when reduced, and $D_{p(tether)reduced}$ represents global ion diffusivity in the poly(TP—OEG-SO$_4$) when reduced. The labels give the numerical values of the ratio. This plot dramatically illustrates the contrast between the ion transport behavior of poly(DMPT) and poly(TP—OEG-SO$_4$) in the reduced states. At high electrolyte concentrations, there is virtually no difference between the two polymers. However, as the electrolyte concentration is lowered to trace levels, an enormous difference emerges wherein D is on the order of 1000-fold slower in the case of poly(TP—OEG-SO$_4$). This difference is heightened to 4522-fold as the scan rate is lowered to 5 mV/sec. This result suggests a model where polymer reduction causes the tethers to be freed, no longer intramolecularly ion-paired to the polymer main chain, which is now neutral. The low electrolyte concentration leaves the tethered sulfonates in a deshielded state, and thus they freely repel one another. This electrostatic driving force that causes them to maximize their distances from one another also causes the tether chains to elongate and encroach into the surrounding nanoscale spaces around the main chain, thus blocking the nanopores and hindering ion diffusion.

A plot of oxidation peak current vs. electrolyte concentration (FIG. 10) allows extrapolation to zero concentration electrolyte, which gives an indication of how much current is supported by, or originates from, ion-pairing of the tether with the polymer backbone that allows release of electrons from the pi-orbital structure of the polymer. FIG. 11 is a plot of the ratio tether-supported current/total current versus scan rate. "Total current" is the peak current at each electrolyte concentration. The values for tether-supported current at each scan rate were obtained from FIG. 10 by linear extrapolation to zero mM electrolyte. FIG. 11 dramatically shows that when electrolyte concentrations are low, the tether supports nearly all of the current (>94%). This result supports the model shown in FIG. 4. At the low scan rate of 5 mV/sec, nearly 97% of the current is supported by the tether. An increase in electrolyte concentration causes the tether to become much less effective at supporting current—at 200 mM electrolyte, it supports only ca. 4% of the total. This effect may arise from competitive or even preferential ion-pairing between the tethered sulfonate and the t-butyl ammonium electrolyte. Such a construction would be very bulky and may even restrict the movement of neighboring tethered sulfonates. This type of ion-pairing may contribute to the pronounced trends seen in FIG. 9, where low electrolyte concentration allowed the tethers to most effectively lower D when the polymer was in the reduced state.

Figure 10:
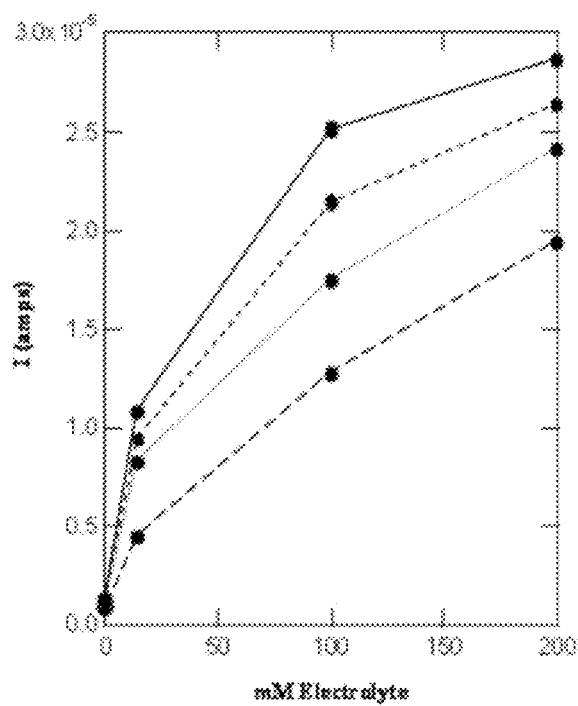
FIG. 10 shows oxidation peak current vs. mM electrolyte. Solid line, scan rate 20 mV/sec; short dashed line, scan rate 15 mV/sec; dotted line, scan rate 10 mV/sec; long dashed line, scan rate 5 mV/sec.
Figure 11:
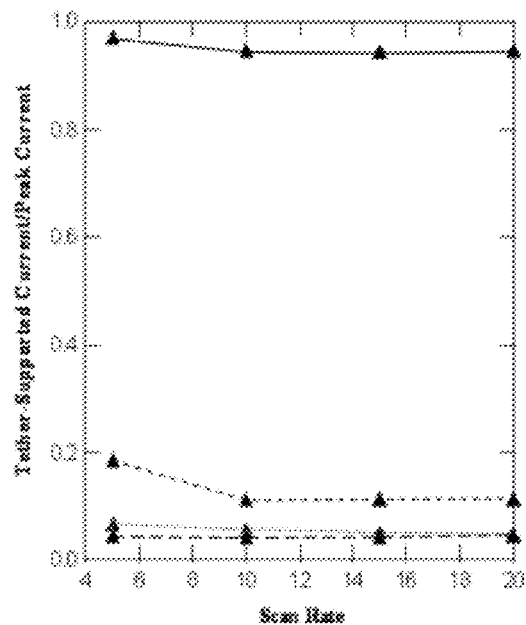
FIG. 11 shows ratio (tether-supported current/total current) vs. scan rate. Solid line, 0.1 mM electrolyte; short dashed line, 14 mM electrolyte; dotted line, 100 mM electrolyte; long dashed line, 200 mM electrolyte.

The evidence presented in FIGS. 7-11 support the mechanism shown in FIG. 4. For both polymer states, FIG. 7 gives the numerical values of the ion diffusivities as functions of electrolyte concentration and scan rates. FIGS. 8 and 9 show how the ratios of these diffusivities vary with changes in electrolyte concentration and scan rates. For poly(TP—OEG-SO$_4$), over a wide range of electrolyte concentrations the ratio $D_{ox}/D_{red}$ converges to a value of 363±1 at low scan rates. The fact that a universal value is reached, independent of electrolyte concentration, implies that the diffusivities are controlled by a process involving mechanical obstruction and clearance, rather than one involving extended ionic interactions such as double-layer formation. The convergence at a low scan rate indicates that this process has a characteristic time of perhaps several minutes. In striking contrast, the poly(DMPT) does not show this behavior at all for any of the electrolyte concentrations studied. FIG. 9 provides evidence that de-shielding of the charged tethers (through lowering of electrolyte concentration) causes them to experience mutual repulsion and extend into adjacent regions, lowering solute diffusivities by as much as 4500-fold. Not surprisingly, the lowest values occur at the slowest scan rates. This is additional evidence that the nanogating process needs a certain amount of time for completion, an amount probably associated with tether chain relaxation and proper organization. FIGS. 10 and 11 clearly show that as electrolyte concentration is lowered to trace amounts, the tethered sulfonate dominates the ion-pairing processes in the polymer that are necessary for electron release and current generation. This suggests that the polymer may be able to produce a nanogating effect in the completely dry state, and become a truly electronic material versus an electrochemical one.

Example 5

Figure 12:
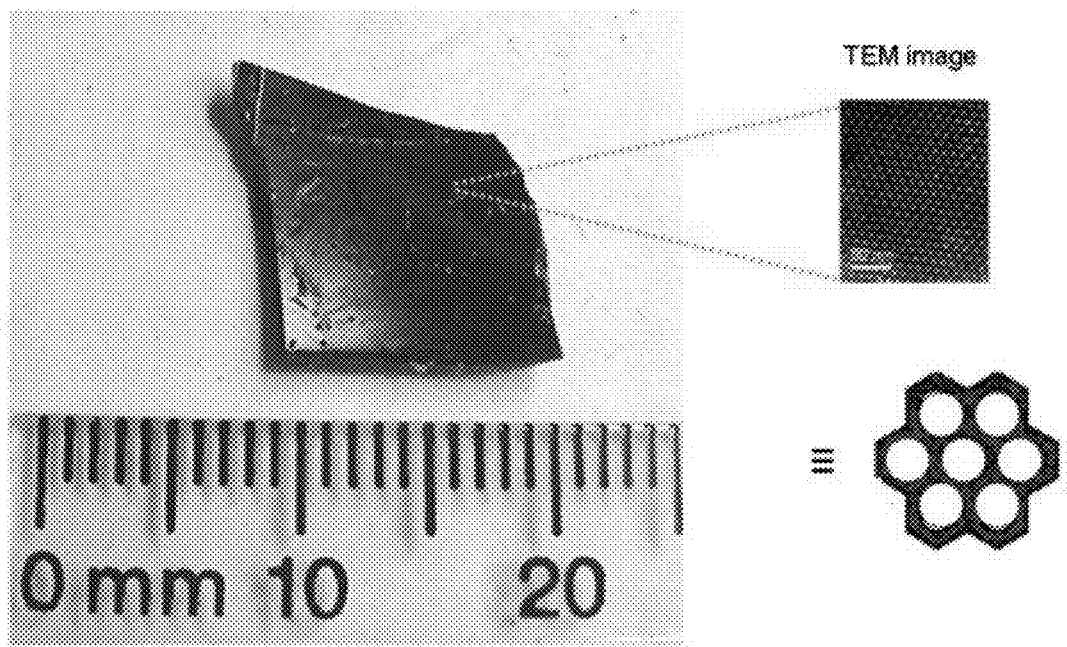
FIG. 12 shows a monolithic sample of an ordered mesoporous C—Si nanocomposite support.

Supercapacitance of poly(TP—OEG-SO$_4$)—To explore the electrochemical and capacitive properties of poly(TP—OEG-SO$_4$), an ordered mesoporous carbon support material was synthesized. This was done following literature procedures (Liu et al., *J. Am. Chem. Soc.* (2006) 128, 11652). The material was monolithic, and was found to have a BET surface area 438 m$^2$/gram, a pore diameter 56 Angstroms, a pore volume of 0.459 cm$^3$/gram, and a very low electrical resistance of ~1 Ohm/mg. A photograph of the material is shown in FIG. 12. Hereafter, the material is represented by the hexagonal symbol shown.

The approach was to electropolymerize a very thin layer of the conducting polymer onto the mesopore walls of the support. If the polymer is formed to high enough MW, the small sizes of the mesopores can be expected to prevent it from diffusing out of the support. It would then be possible to cycle the polymer between its oxidized (doped) and reduced (dedoped), and monitor its capacitive response.

Figure 13:
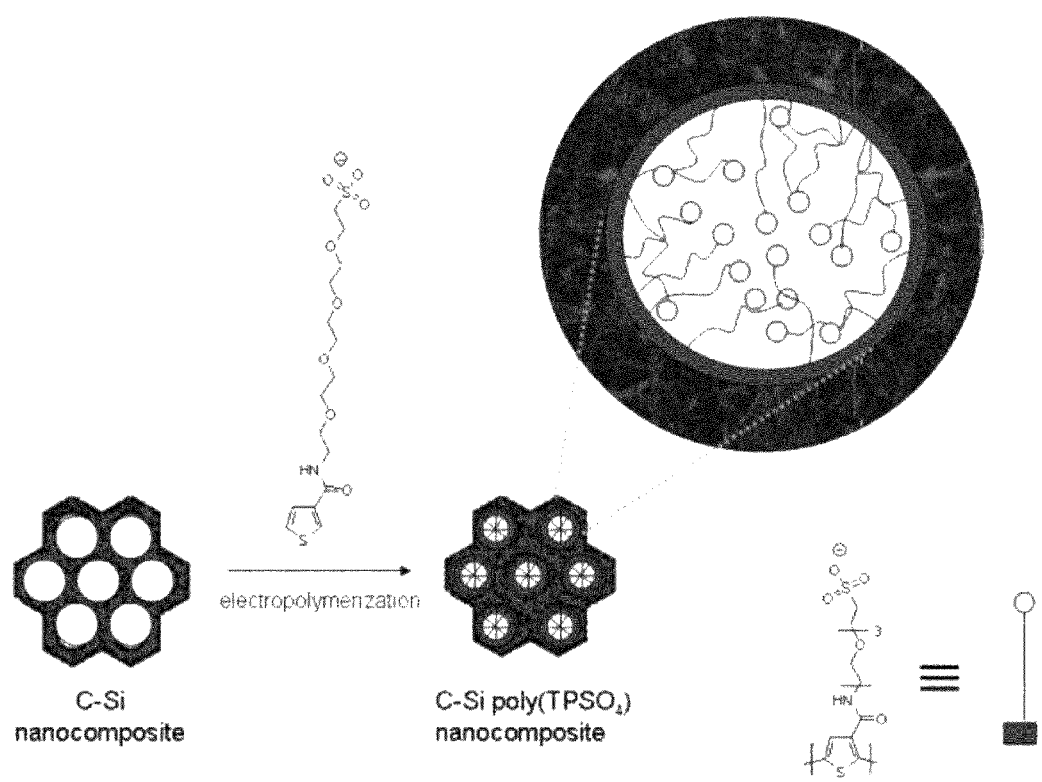
FIG. 13 shows electropolymerization of poly(TP—OEG-SO$_4$) onto the mesopore walls of the C—Si conducting nanocomposite.

Prior to electropolymerization, 33 mg of TP—OEG-SO$_4$ was dissolved in acetonitrile containing 100 mM LiClO$_4$ electrolyte. A C—Si monolith sample of mass 23.9 mg was immersed in this solution for 16 hrs. The monomer-impregnated sample was then removed from solution, re-immersed into a fresh electrolyte solution containing 100 mM LiClO$_4$ and subjected to a potential of 1.8 volts vs. Ag/AgCl for 15 seconds. This caused the monomer to be electropolymerized within the mesopores as expected, presumably as a thin layer on the mesopore walls with the tether moieties extending outward (FIG. 13). Chronocoulometry and thermogravimetric analysis showed that 0.22 mg poly(TP—OEG-SO$_4$) had formed within the support.

Figure 14:
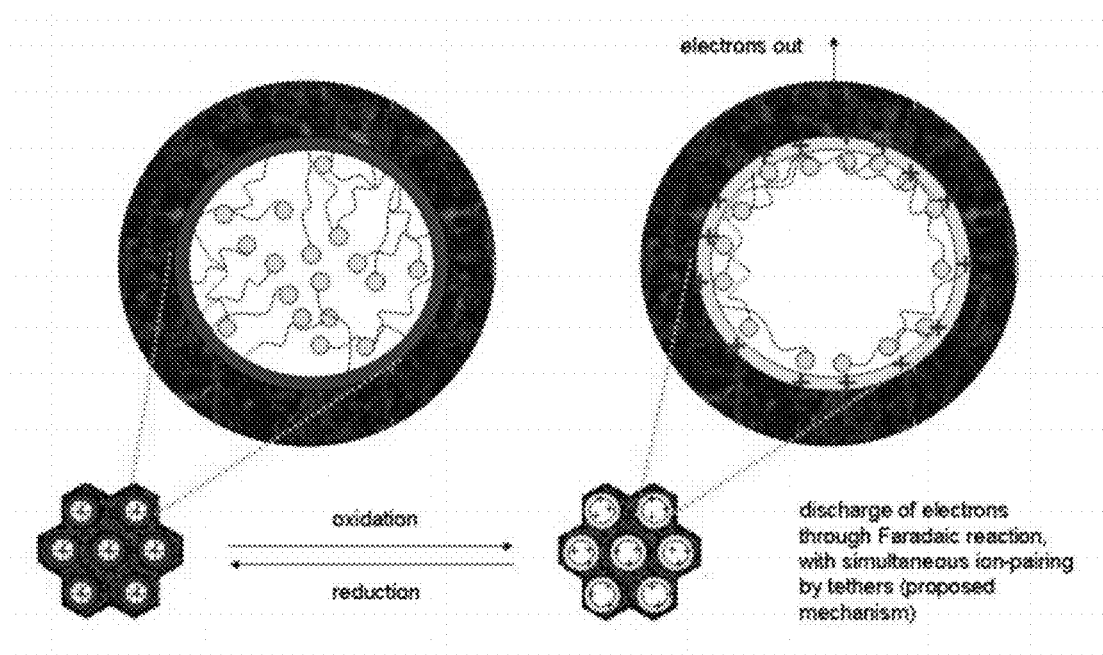
FIG. 14 shows redox reaction of poly(TP—OEG-SO$_4$) occurring during cyclic voltammetry.

FIG. 14 depicts the redox reaction of poly(TP—OEG-504) that occurs during cyclic voltammetry, and the proposed intramolecular ion-pairing by the sulfonate tethers that accompanies the release of electrons from the pi-orbitals of the conducting polymer main chains. In an electrochemical capacitor, this type of charge release is termed "Faradaic". Charge storage/release through Faradaic processes often exceeds that of simple double-layer processes by as much as one order of magnitude. The polymer tethers may allow an efficient, rapid discharge of current since the anionic tether end-group is only a few nm distant from the cationic center on the conducting polymer main chain that it serves to neutralize. Thus the requirement for long-range diffusion of free electrolyte (for polymer charge neutralization) is greatly diminished. Also, the intramolecular ion-pairing is likely to exhibit some of the diffusion nanogating effects described in the previous section.

Figure 15:
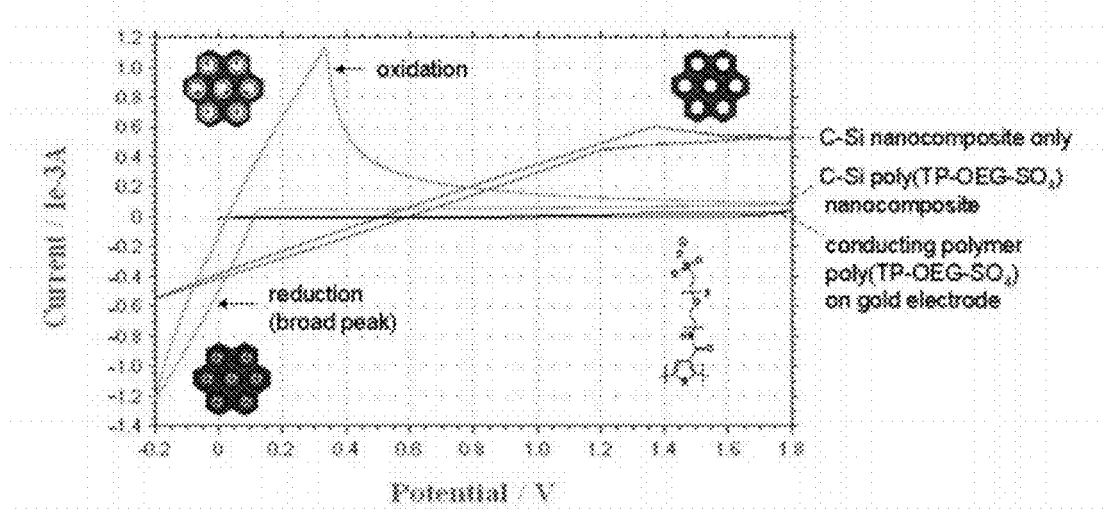
FIG. 15 shows cyclic voltammetry of poly(TP—OEG-SO$_4$) on gold electrode (blue trace), C—Si nanocomposite itself (green), and the C—Si-poly(TP—OEG-SO$_4$) nanocomposite (orange) in oxidized (top) and reduced (bottom) states.
Figure 16:
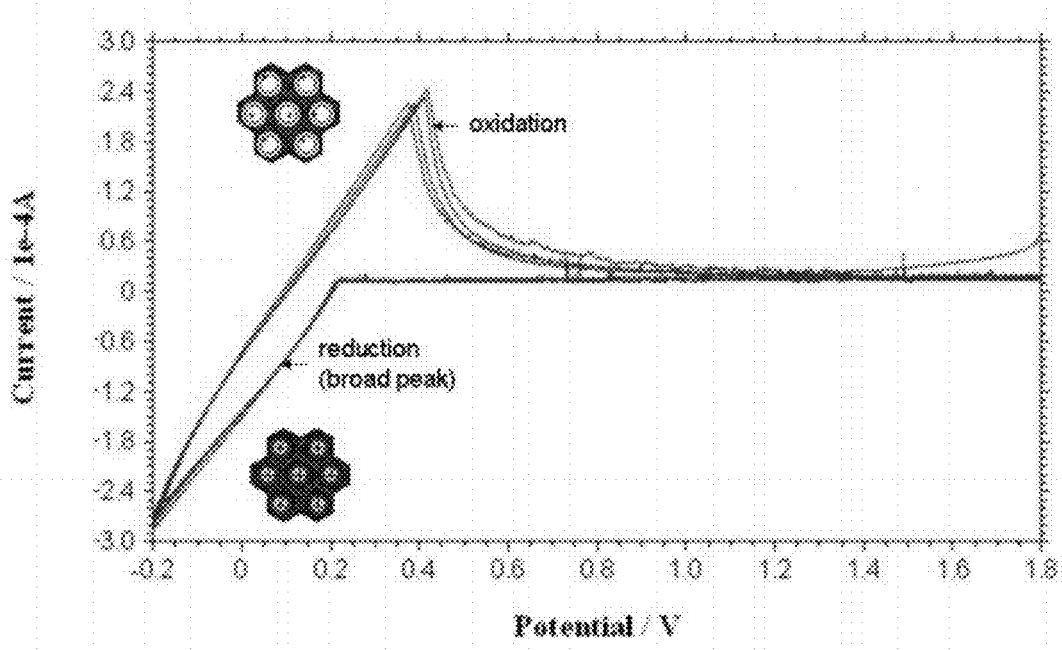
FIG. 16 shows cyclic voltammetry data for C—Si-(TP—OEG-SO$_4$) nanocomposite.

FIG. 15 shows cyclic voltammetry of poly(TP—OEG-SO$_4$) itself on a gold electrode (blue trace), the C—Si nanocomposite itself (green trace), and the C—Si-poly(TP—OEG-SO$_4$) nanocomposite (orange trace) in oxidized (top) and reduced (bottom) states (scan rate 20 mV/sec, electrolyte is 100 mM LiClO$_4$ in acetonitrile). In the latter, the maximum observed currents ($1.2 \times 10^{-3}$ A and $1.2 \times 10^{-3}$ A) are ~40-fold higher than poly(TP—OEG-SO$_4$) alone, and ~2-fold higher than that exhibited by the C—Si nanocomposite. The effect of the poly(TP—OEG-SO$_4$) in the nanocomposite is clearly seen by comparing the green and orange traces. It was found that the unusually sharp oxidation peak is a general characteristic of the C—Si-poly(TP—OEG-SO$_4$) nanocomposites. FIG. 16 shows the cyclic voltammetry data for the 23.9 mg C—Si-(TP—OEG-SO$_4$) nanocomposite with 0.22 mg poly(TP—OEG-SO$_4$) formed on the mesopore walls by electropolymerization for 15 seconds at 1.8 V vs. Ag/AgCl (scan rate 2 mV/sec, electrolyte 100 mM LiClO$_4$ in acetonitrile). For the oxidation peak, the capacitance was calculated using the relation capacitance=integrated average current/scan rate. This yields a specific capacitance value of 2570 farads/gram poly(TP—OEG-SO$_4$)·M electrolyte.

Figure 17:
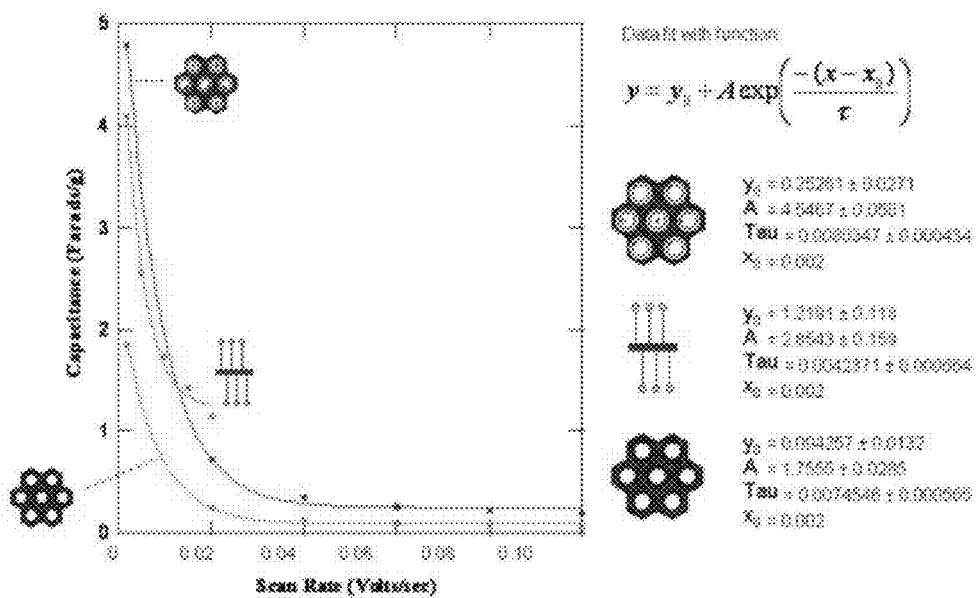
FIG. 17 shows total capacitance vs. scan rate (V/sec) for the oxidation reaction of poly(TP—OEG-SO$_4$).
Figure 18:
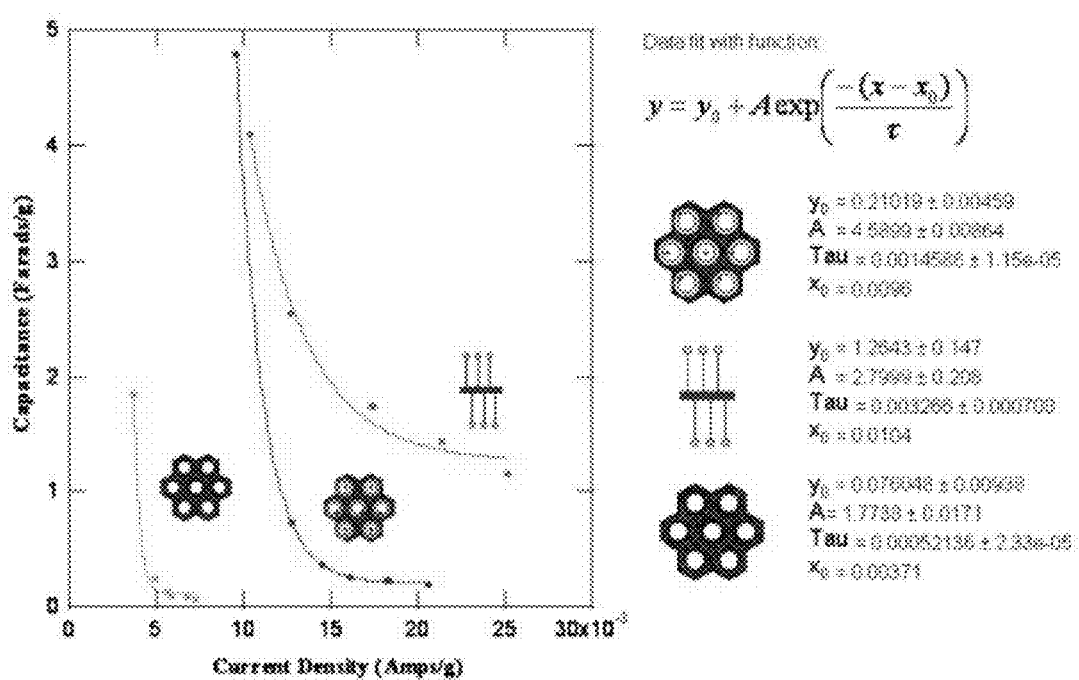
FIG. 18 shows total capacitance vs. current density (Amps/g) for the oxidation reaction of poly(TP—OEG-SO$_4$)

FIG. 17 shows total capacitance vs. scan rate (V/sec) for the oxidation reaction of poly(TP—OEG-SO$_4$) on a gold electrode (blue curve), the C—Si nanocomposite itself (green curve), and the C—Si-poly(TP—OEG-SO$_4$) nanocomposite (red curve) (electrolyte 100 mM LiClO$_4$ in acetonitrile). The asymptotic, exponential increase in capacitance as the scan rate approaches zero may arise because the tethers need a certain minimum time to become organized, either to intramolecularly ion-pair with cationic centers on the polymer chain, allow passage of free electrolyte, or to organize free electrolyte into charge-storing structures. The data is fit with the function $y=y_0+A\exp(-(x-x_0)/\tau)$. FIG. 18 gives total capacitance vs. current density (Amps/g) for the oxidation reaction of poly(TP—OEG-SO$_4$) on a gold electrode (blue curve), the C—Si nanocomposite itself (green curve), and the C—Si-poly(TP—OEG-SO$_4$) nanocomposite (red curve) (electrolyte 100 mM LiClO$_4$ in acetonitrile). The asymptotic increase in capacitance as the current density approaches zero is consistent with the trend shown for scan rate in FIG. 17. For poly(TP—OEG-SO$_4$) on the gold electrode—from left to right, each of the five data points corresponds to scan rates of 0.002, 0.005, 0.01, 0.015, and 0.02 V/sec. For the C—Si nanocomposite itself and the C—Si-poly(TP—OEG-SO$_4$)—from left to right, each of the five data points corresponds to scan rates of 0.002, 0.02, 0.03, 0.04, and 0.05 V/sec. The data is fit with the function $y=y_0+A\exp(-(x-x_0)/\tau)$.

Figure 19:
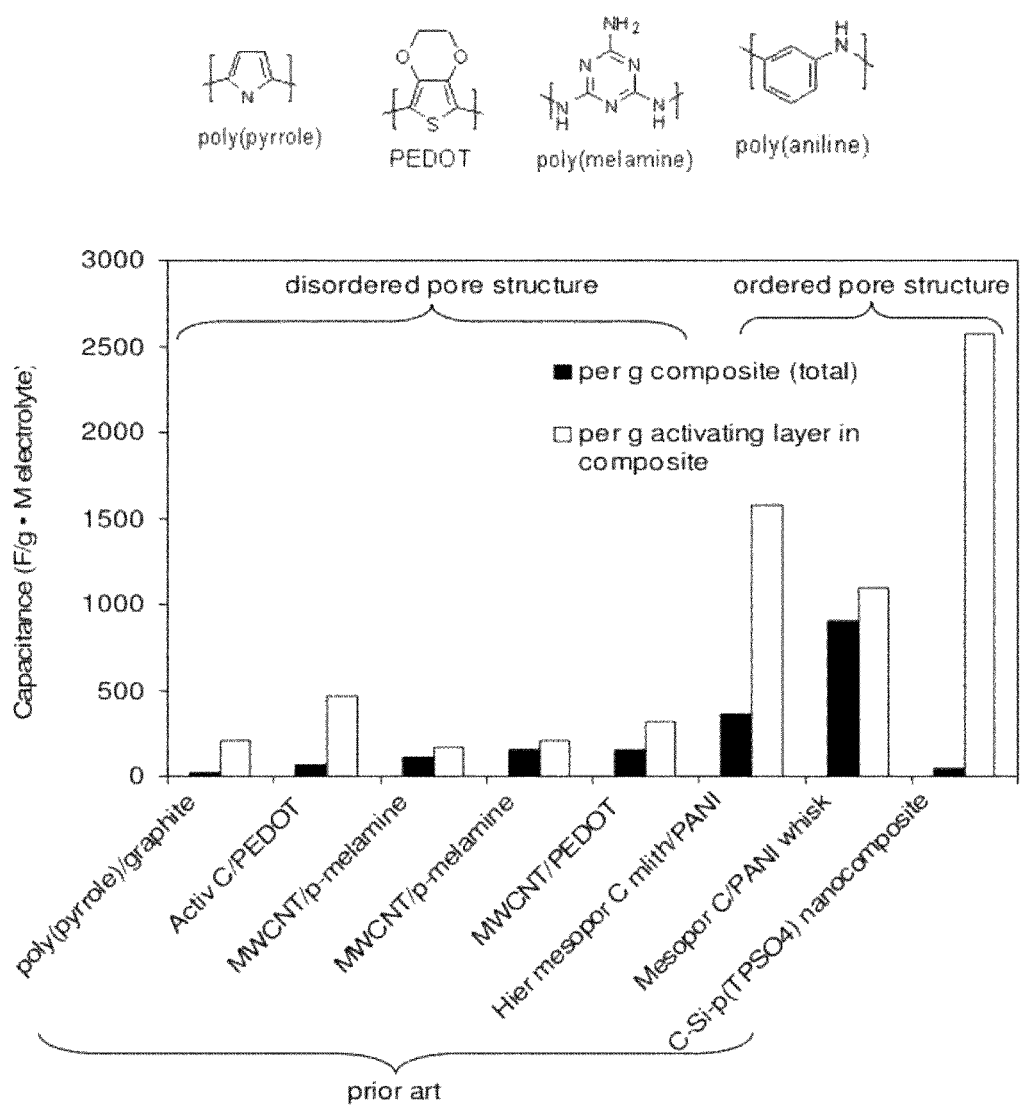
FIG. 19 shows supercapacitances of C—Si-poly(TP—OEG-SO$_4$) nanocomposite and of materials based on conventional conducting polymers in mesoporous carbon supports (from literature up to 2008). "Activ C" denotes activated carbon; "PEDOT" denotes poly(3,4-ethylenedioxythiophene); "MWCNT" denotes multiwalled carbon nanotubes, "Hier mesopor C" denotes hierarchically-ordered mesoporous carbon; "PANI" denotes polyaniline; "Mesopor C" denotes mesoporous carbon.

FIG. 19 shows supercapacitances of C—Si-poly(TP—OEG-SO$_4$) nanocomposite and of materials based on conventional conducting polymers in mesoporous carbon supports (from literature up to 2008). The figure that includes the values for total capacitance of the C—Si-poly(TP—OEG-SO$_4$) nanocomposite (48 farads/g·M electrolyte), and the specific capacitance of poly(TP—OEG-SO$_4$) (2570 farads/g·M electrolyte). For all materials, the value shown is the highest value reported for the material studied.

Example 6

Synthesis of Nanogating IPN—The supported IPN was synthesized by blending a polyurethane-containing solvent with a second solvent containing TP—OEG-SO$_4$ and an iron (III) tosylate oxidant, heating the mixture, and casting it into support filters. Support materials included microporous PTFE (Teflon) filters having an average pore size of 0.45 microns with a thickness of 30 microns, and nanoporous PES (polyethersulfone) having an average pore size of 0.03 microns with a thickness of 60 microns.

For example, 240 µL of THF containing 10 wt % Estane MVT 75 polyurethane (BF Goodrich) was added to 160 µL anisole containing 6 mg EDOT crosslinker, forming solution "1". The mixing was performed in a 20 mL vial. Next, 140 µL ethanol containing 24 mg TP—OEG-SO$_4$ was added to 200 µL ethanol containing 120 mg iron (III) tosylate oxidant, forming solution "2", again in a 20 mL vial. Solutions 1 and 2 were then mixed vigorously (2 was added to 1), and heated for 60 seconds in an oven, temperature 75° C. To permit full solubility of the polyurethane component, an additional 160 µL THF was added with mixing and the solution was allowed to heat for an additional 30 seconds. Finally, three 180 µL aliquots of the solution were then deposited onto three PES filter sections of dimensions 2.25 cm×2.25 cm (the sections were resting on a glass microscope slide). The deposition was done by pipette, in a rapid manner (2-3 seconds per filter section) because slower solvent delivery from the pipette tended to cause the final filter-supported IPN to have pinholes. The glass slide with the solution-impregnated filter sections were then placed in the oven at 75° C., and the polymerization proceeded overnight. The IPN formed in the filter support and was dark blue in color because of the oxidized poly(TP—OEG-504). The samples were carefully removed from the glass slide and immersed in hot water for 10 seconds (stirring, 85° C.) to extract the iron (II) reaction byproduct as well as any unreacted iron (III) and TP—OEG-SO$_4$. The samples were then air-dried and stored at room temperature. For a given sample, transformation of the poly(TP—OEG-SO$_4$) portion of the IPN from its as-synthesized "doped" oxidized state to its reduced "dedoped" state was accomplished by using a dilute (3 wt %) hydrazine solution in ethanol. The sample was immersed in the solution for 30 minutes with stirring, the residual hydrazine was removed by washing in pure ethanol, and the sample was air-dried at room temperature and stored under nitrogen. (This transformation may also be performed electrochemically.)

For diffusion studies using methyl parathion, the samples were fixed into a horizontal 2-chambered diffusion cell (Peremegear, Bethlehem Pa.), with careful use of a small amount of vacuum grease for sealing. A solution of methyl parathion (MP) in ethanol (0.1 mg/mL) was added to the left-hand (feed) chamber, and pure ethanol was added to the right-hand (receiving) chamber. Each chamber had a volume of 3.4 mL. The mass transfer area between the two chambers was 0.74 cm$^2$. As the diffusion proceeded, 50 µL aliquots of solution were removed from the receiving chamber at set time intervals. To provide an internal standard for GC-MS analysis, a solution containing 10 mg/mL anthracene in benzene was prepared and 1 µL was then added to 940 µL acetone. Each 50 µL aliquot from the receiving chamber was then added to the 950 µL acetone/hexane/anthracene solution, and thoroughly mixed. Finally, 1 μL of the latter solution was injected into the GC-MS apparatus (Shumadzu, Baltimore Md.) for analysis.

Figure 20:
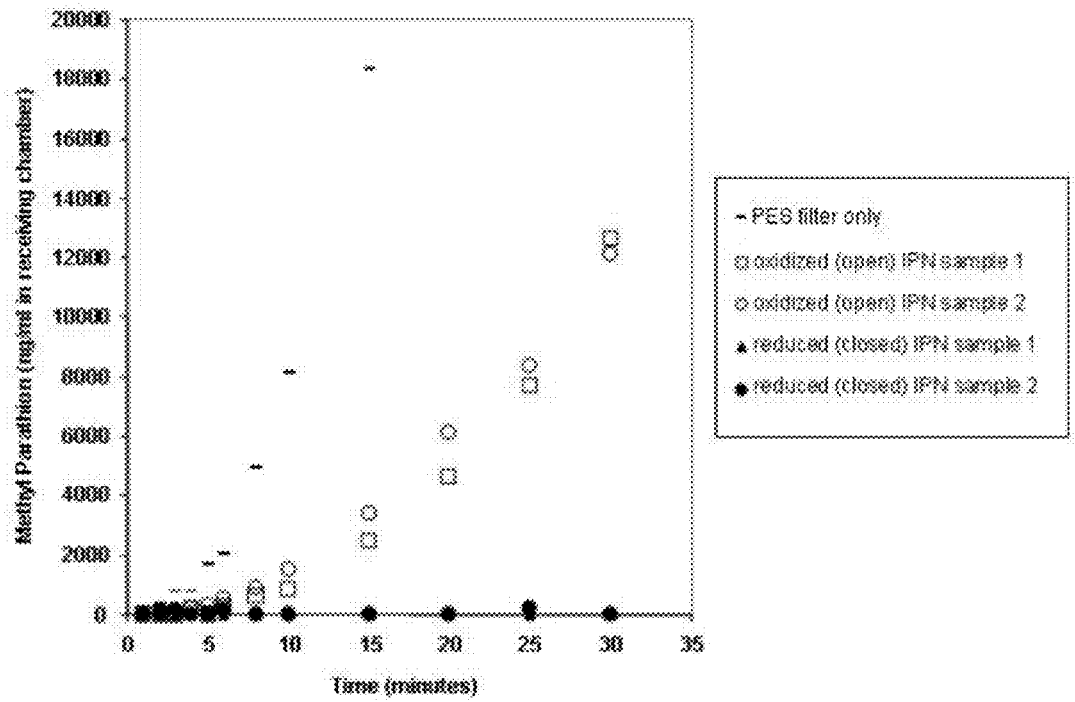
FIG. 20 shows the time-dependent diffusion behavior of methyl parathion (MP) in the IPN/PES filter and PES filter alone. Concentrations of MP are reported in ng/mL of solution in the receiving chamber.

The time-dependent diffusion behavior of methyl parathion in the IPN/PES filter and filter alone is seen in FIG. 20, Table 1, and Table 2. Concentrations of MP are reported in ng/mL of solution in the receiving chamber. Clearly, the oxidized "open" state of the IPN permits the MP to pass through much more rapidly than the reduced "closed" state. The feed chamber contains $1 \times 10^5$ ng/mL MP, and by t=30 minutes the "open" state has permitted the receiving chamber to reach a concentration of $\sim 1.2 \times 10^4$ ng/mL MP, or nearly 10% of the value of the feed chamber. In contrast, the closed state permitted the receiving chamber to reach only much lower concentrations. These are difficult to discern from FIG. 20 since they are very near zero. The values are included in Table 1, and they lie very near the lower detection limit of the GC-MS apparatus. The average of these tabulated values is ~31 ng MP/mL in the receiving chamber. Thus, by t=30 minutes the ratio of the MP concentrations that appear in the receiving chamber via the open state to the concentrations that appear in the receiving chamber via the closed state is $1.2 \times 10^4/31$, or ~390. Table 2 gives this ratio for times between zero and 30 minutes. Over the 30 minute time period, the amount that passed through the closed state was ~100 ng. It originated from a feed chamber that contained 0.340 mg at the start of the experiment.

TABLE 1

Tabulated values describing the time-dependent diffusion behavior of methyl parathion (MP) in the IPN/PES filter and PES filter alone. Concentrations of MP are reported in ng/mL of solution in the receiving chamber

| t (min) | PES filter only | reduced sample 1 (closed state) | reduced sample 2 (closed state) | oxidized sample 1 (open state) | oxidized sample 2 (open state) |
|---|---|---|---|---|---|
| 1 | 180 | 0 | 0 | 0 | 0 |
| 2 | 380 | 0 | 120 | 0 | 0 |
| 3 | 800 | 0 | 180 | 0 | 0 |
| 4 | 800 | 0 | 0 | 220 | 200 |
| 5 | 1660 | 0 | 0 | 0 | 320 |
| 6 | 2040 | 0 | 160 | 260 | 520 |
| 8 | 4940 | 0 | 0 | 640 | 880 |
| 10 | 8160 | 100 | 0 | 820 | 1540 |
| 15 | 18320 | 0 | 0 | 2440 | 3420 |
| 20 | 32900 | 0 | 0 | 4600 | 6120 |
| 25 | 49960 | 0 | 220 | 7660 | 8360 |
| 30 | 87120 | 0 | 0 | 12620 | 12120 |

TABLE 2

The time-dependent ratio of the MP concentrations that appear in the receiving chamber via the open state to the concentrations that appear in the receiving chamber via the closed state

| t (min) | avg | std dev |
|---|---|---|
| 1 | 0 | 0 |
| 2 | 0 | 0 |
| 3 | 0 | 0 |
| 4 | 6.8 | 0.3 |
| 5 | 5.2 | 5.2 |
| 6 | 12.6 | 4.2 |
| 8 | 24.5 | 3.9 |
| 10 | 38.1 | 11.6 |
| 15 | 94.5 | 15.8 |
| 20 | 172.9 | 24.5 |
| 25 | 258.4 | 11.3 |
| 30 | 398.7 | 8.4 |

Example 7

Ion diffusivities using electrochemical impedance spectroscopy with cyclic voltammetry—The ion diffusivities in the IPNs were determined using a form of electrochemical analysis that measures the electrical response of the material as it is subjected to alternating currents of variable frequencies ranging from millions of cycles per second (MHz) to less than one cycle per second (Hz). This method of analysis is termed electrochemical impedance spectroscopy (EIS), and it is quite powerful in that it simultaneously provides measurements of interfacial charge-transfer resistance, ion diffusivities, and capacitive (charge-storage) effects. The instrumentation provides correlations between the real component of the impedance of the material (denoted as Z') and other parameters such as frequency and phase angle. Plots of Z' vs. $1/\text{frequency}^{0.5}$ depict correlations with positive slopes. The slope in any given region (often termed the Warburg coefficient) is inversely proportional to the ion diffusivity in the material. This provides another means of measuring these diffusivities.

Figure 21:
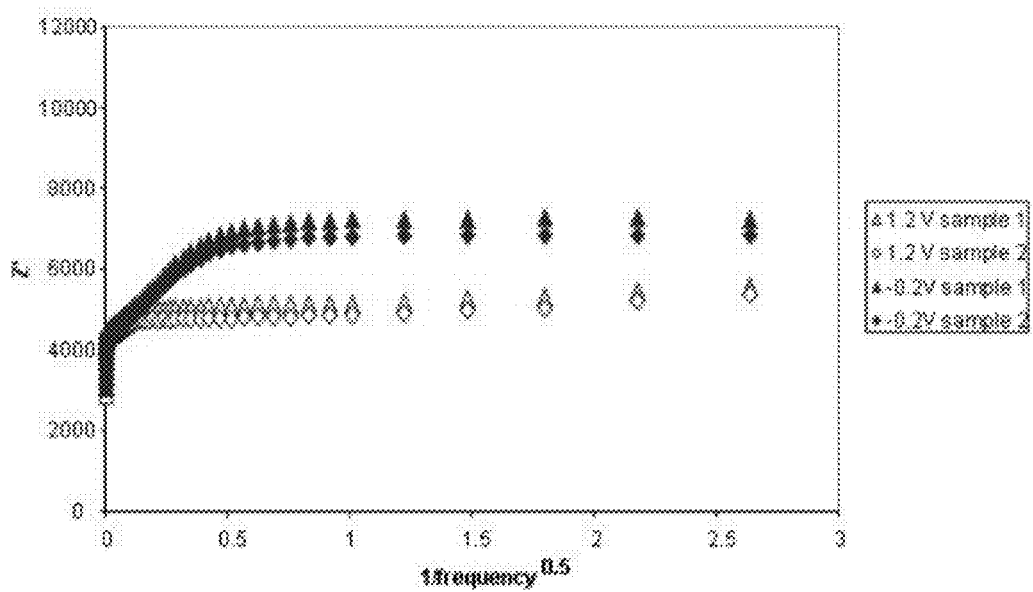
FIG. 21 shows a plot of the real component of the impedance (Z') vs 1/frequency$^{0.5}$ for IPNs in the oxidized and reduced states.

FIG. 21 shows an example of a plot of Z' vs. $1/\text{frequency}^{0.5}$ for the IPN supported by a PTFE filter. For each experiment, the frequency was varied from 0.1 MHz to 0.01 Hz. The wave amplitude was 10 mV. Experiments were performed when the material was in its oxidized (open-pore) state, and also when the material was in its reduced (closed-pore) state. To create the former state, the sample was held at 1.2 volts (vs. Ag wire); for the latter, it was held at −0.2 volts. The overall slopes of the plots indicate that the global diffusivity of the electrolyte (including the sulfonate tether) is lower when the polymer is reduced vs. oxidized.

The following relationship (the Warburg equation) was used to calculate the ion diffusivity D from knowledge of the Warburg coefficient and the parameters T (temperature), F (Faraday's constant), A (area of the sample), n (number of electrons in the reaction mechanism, calculated from cyclic voltammetry data), and C (electrolyte concentration in mol/cm$^3$).

$$D = \left[\frac{2RT}{n^2 F^2 CA\sigma\sqrt{2}}\right]^2$$

Figure 22:
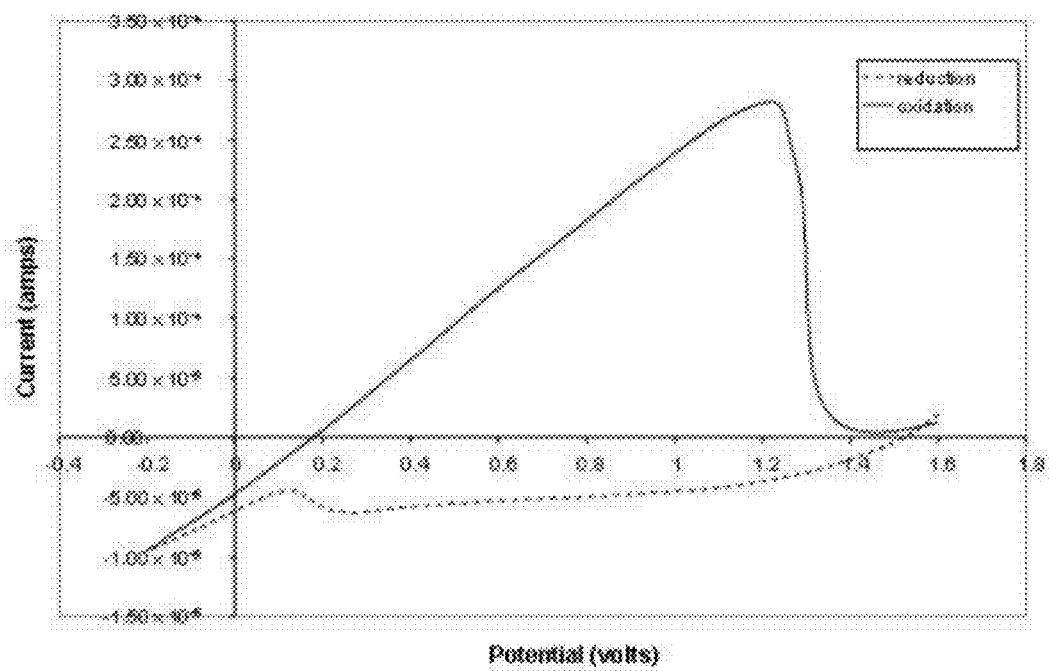
FIG. 22 shows a cyclic voltammogram of IPN, scan rate 20 mV/sec.

An example of the cyclic voltammetry data of the IPN (used to calculate n) is given in FIG. 22. For this experiment, a scan rate of 20 mV/second was used, and the IPN was supported by a PTFE filter. Using the Randles-Sevcik equation, the resulting values for D are $1.40 \times 10^{-6}$ cm$^2$/sec (scan rate 10 mV/second) and $9.72 \times 10^{-6}$ cm$^2$/sec (scan rate 20 mV/second) for the material in its oxidized (open-pore) state, and $6.30 \times 10^{-9}$ cm$^2$/sec (scan rate 10 mV/second) and $1.89 \times 10^{-8}$ cm$^2$/sec (scan rate 20 mV/second) for the material in its reduced (closed-pore) state. Using the Warburg equation, the resulting values for D are $1.92 \times 10^{-6}$ cm$^2$/sec (scan rate 10 mV/second) and $4.76 \times 10^{-6}$ cm$^2$/sec (scan rate 20 mV/second) for the material in its oxidized (open-pore) state, and $1.97 \times 10^{-9}$ cm$^2$/sec (scan rate 10 mV/second) and $7.37 \times 10^{-9}$ cm$^2$/sec (scan rate 20 mV/second) for the material in its reduced (closed-pore) state.

Figure 23:
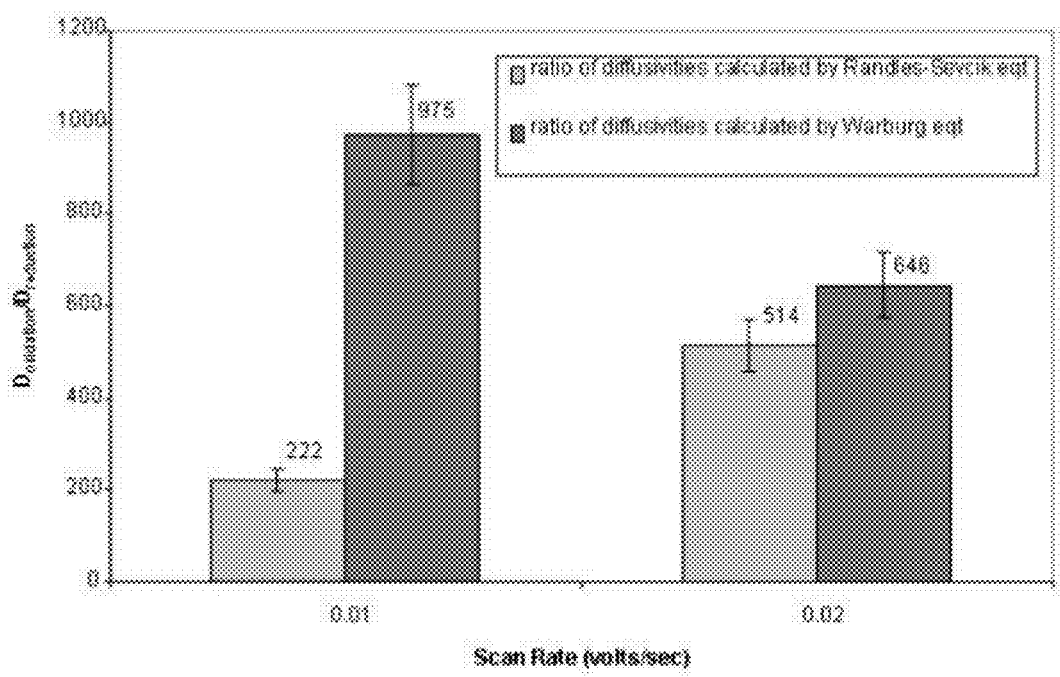
FIG. 23 shows the ratios of ion diffusivities in the oxidized and reduced states of the IPN, as a function of cyclic voltammetry scan rate.

The ratios of the ion diffusivities in the oxidized state to the ion diffusivities in the reduced state ($D_{oxidized}/D_{reduced}$) are plotted in FIG. 23 as a function of scan rate, and they range from 222 to 975. Therefore ion diffusivities in the IPN are from 222 to 975-fold slower when the material is in its closedvs. open-pore state. This constitutes further proof that the IPN is able to act as a "nanogate" for control of solute diffusion.

Example 8

Figure 24:
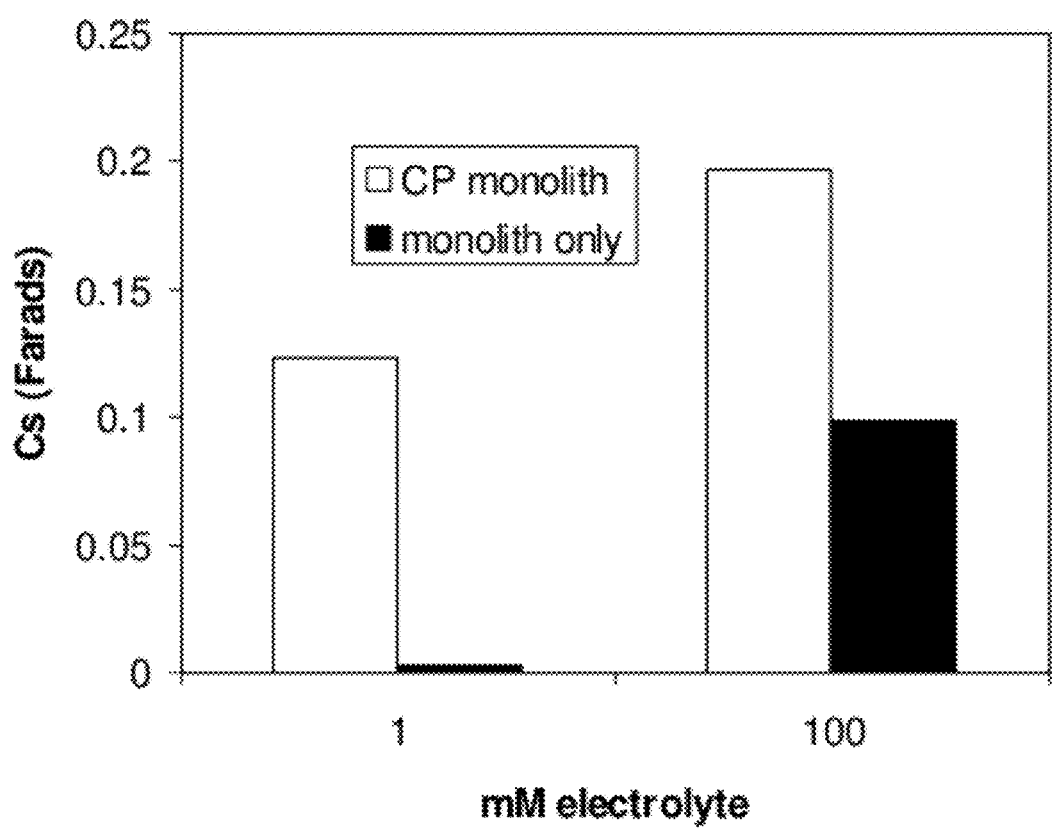
FIG. 24 shows the Faradaic capacitance $C_s$ of C—Si-(TP—OEG-SO$_4$) nanocomposite (denoted as "CP monolith" and the C—Si monolith alone, at two different electrolyte concentrations. Error bars are ~6%.

Measurement of the Faradaic capacitance ($C_s$) of the C—Si-(TP—OEG-SO$_4$) nanocomposite and the C—Si monolith alone using electrochemical impedance spectroscopy Electrochemical impedance spectroscopy (wave amplitude was 10 mV) was used to measure the Faradaic capacitance ($C_s$) of a C—Si-(polyTP—OEG-SO$_4$) nanocomposite that was formed by electropolymerization of TP—OEG-SO$_4$ for 15 seconds at 1.8 V vs. Ag wire (electrolyte 100 mM tetrabutylammonium hexafluorophosphate in acetonitrile). The capacitance was measured at two different electrolyte concentrations, 100 mM and 1 mM tetrabutylammonium hexafluorophosphate in acetonitrile. The capacitance of the C—Si monolith alone was also measured at these two electrolyte concentrations. The capacitance determinations were made by plotting the real component of the impedance (Z') vs. 1/frequency$^{0.5}$, and measuring the slope, which is equal to the Warburg coefficient $\sigma$. $C_s$ was then found from the relation $C_s=1/(\sigma \cdot \text{frequency}^{0.5})$. The results are shown in FIG. 24. At 100 mM electrolyte, the presence of the poly(TP—OEG-SO$_4$) increases the capacitance $C_s$ of the nanocomposite by a factor of about 2 relative to the monolith alone. When the electrolyte concentration is reduced to 1 mM, the presence of the poly(TP—OEG-SO$_4$) allows the composite to maintain a very high $C_s$ vs. the monolith alone, one that is higher by a factor of 0.123/0.0027 or 46. This is evidence of a charge-storage mechanism that features the negatively-charged sulfonate of the poly(TP—OEG-SO$_4$) forming an intramolecular ion-pair with the positive charge centers in the conducting polymer backbone. The electrolyte salt evidently has little or no involvement in the capacitive charge storage. It is possible that the material may be able to maintain a high $C_s$ in the totally dry state, in the complete absence of electrolyte.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A compound having the formula:

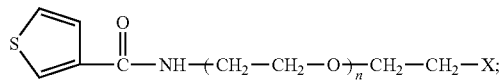

wherein X is hydroxyl, a sulfonic ester or salt thereof, a phosphonate or salt thereof, a carboxylate or salt thereof, or a boronic ester or salt thereof; and
wherein n is an integer greater than or equal to 2.

2. The compound of claim 1, wherein n is from 2 to 10.

3. The compound of claim 1, wherein the compound is:

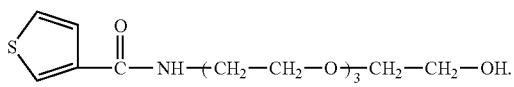

4. The compound of claim 1, wherein the compound is:

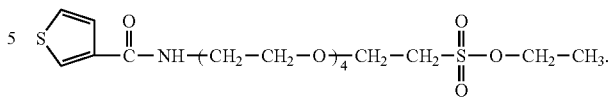

5. The compound of claim 1, wherein the compound is:

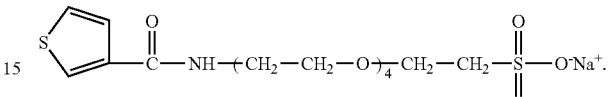

6. A polymer made by polymerizing a compound having the formula:

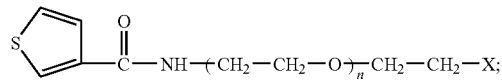

wherein X is a sulfonate salt, a phosphonate salt, a carboxylate salt, or a boronate salt; and
wherein n is an integer greater than or equal to 2.

7. The polymer of claim 6, wherein the compound is:

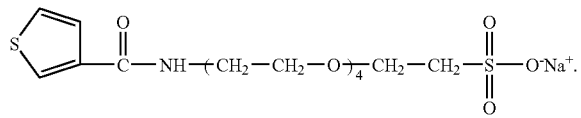

8. The polymer of claim 6, wherein the polymer is:

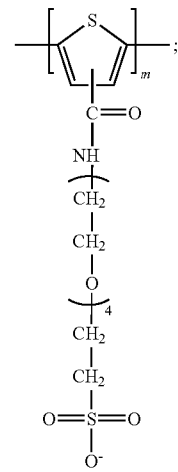

wherein m is a positive integer.

9. The polymer of claim 6, wherein the polymer is:

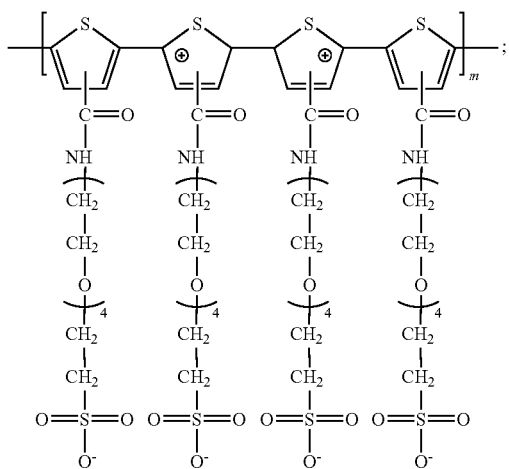

wherein m is a positive integer.

10. The polymer of claim 6, wherein the polymer is made by copolymerizing the compound with a second monomer of a conducting polymer.

11. The polymer of claim 10, wherein the second monomer is thiophene or a substituted thiophene.

12. A capacitor comprising:
an anode;
a cathode; and
a material comprising the polymer of claim 6 between the anode and the cathode.

13. A method comprising:
applying an oxidizing voltage to a material comprising the polymer of claim 6;
whereby the diffusivity of the material is increased; and
applying a reducing voltage to the material;
whereby the diffusivity of the material is decreased.

14. A method comprising:
reacting $NH_2$—$(CH_2$—$CH_2$—$O)_n$—$CH_2$—$CH_2$—$OH$ with thiophene acid chloride to form a $(SC_4H_3)$—$CO$—$NH$—$(CH_2$—$CH_2$—$O)_n$—$CH_2$—$CH_2$—$OH$ amide;
wherein n is an integer greater than or equal to 1;
reacting the amide with a vinyl sulfonic ester, a vinyl phosphonate, a vinyl carboxylate, or a vinyl boronic ester to form an intermediate; and
converting the intermediate to a salt form.

15. The method of claim 14, wherein n is from 1 to 9.

16. The method of claim 14, wherein the intermediate is:

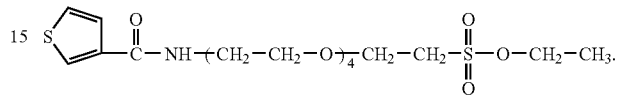

17. The method of claim 14, wherein the salt form is:

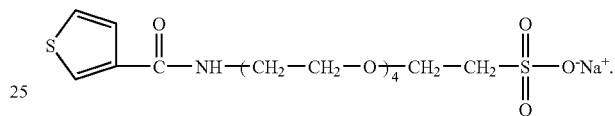

18. The method of claim 14, further comprising:
polymerizing the salt form.

19. The method of claim 18, wherein the polymerization is a copolymerization with a second monomer of a conducting polymer.

20. The method of claim 19, wherein the second monomer is thiophene or a substituted thiophene.

* * * * *